(12) United States Patent
Weadock et al.

(10) Patent No.: US 10,376,674 B2
(45) Date of Patent: Aug. 13, 2019

(54) SYSTEM AND METHOD FOR TARGETED DELIVERY OF THERAPEUTIC AGENTS TO TISSUE

(71) Applicant: Ethicon, Inc., Somerville, NJ (US)

(72) Inventors: Kevin Weadock, Hillsborough, NJ (US); Jeffrey Hammond, Bernardsville, NJ (US)

(*) Notice: Subject to any disclaimer, the term of this patent is extended or adjusted under 35 U.S.C. 154(b) by 406 days.

(21) Appl. No.: 14/485,853

(22) Filed: Sep. 15, 2014

(65) Prior Publication Data

US 2016/0074626 A1 Mar. 17, 2016

(51) Int. Cl.
*A61B 17/34* (2006.01)
*A61M 25/01* (2006.01)
(Continued)

(52) U.S. Cl.
CPC ........... *A61M 25/0169* (2013.01); *A61B 1/04* (2013.01); *A61B 1/06* (2013.01); *A61B 17/3421* (2013.01); *A61B 17/3468* (2013.01); *A61B 90/39* (2016.02); *A61K 31/282* (2013.01); *A61K 31/337* (2013.01); *A61K 31/4375* (2013.01); *A61K 31/513* (2013.01); *A61K 31/704* (2013.01); *A61K 31/7068* (2013.01); *A61K 33/24* (2013.01); *A61K 38/385* (2013.01);
(Continued)

(58) Field of Classification Search
CPC ........... A61M 25/0169; A61B 17/3468; A61N 2005/1021
See application file for complete search history.

(56) References Cited

U.S. PATENT DOCUMENTS 5,234,426 A 8/1993 Rank et al.
5,855,554 A 1/1999 Schneider et al.
(Continued)

FOREIGN PATENT DOCUMENTS

EP 1658820 5/2006
GB 2422550 8/2006
(Continued)

OTHER PUBLICATIONS

Mayo, J. et al. Lung Nodules: CT-Guided Placement of Microcoils to Direct video-assisted Thoracoscopic surgical Resection; 2009; Radiology, vol. 250, Issue 2, pp. 576-585.
(Continued)

*Primary Examiner* — Thaddeus B Cox
(74) *Attorney, Agent, or Firm* — Melissa J. Szanto

(57) ABSTRACT

Novel systems for and methods of delivering therapeutic agents to target tissues are disclosed. The method of delivering a therapeutic agent to a target tissue involves identifying a target tissue via an imaging modality and then using a guidewire capable of anchoring in tissue to advance a cannula to the target tissue. The guidewire and novel cannula configurations enable rapid and repeated treatments of the target tissue without the need for subsequent imaging. The cannula is coupled to a source of ultrasound, radiation, radiofrequency energy, or chemotherapeutic agents which can then be delivered to from the cannula the target tissue. The system and method can be used to treat tumors that are small or surgically inoperable. In addition, the system can be used to treat lymphatic tissue that may contain metastases from the tumors.

6 Claims, 20 Drawing Sheets

(51) Int. Cl.

| | |
|---|---|
| *A61N 5/10* | (2006.01) |
| *A61K 31/7068* | (2006.01) |
| *A61K 31/513* | (2006.01) |
| *A61K 31/4375* | (2006.01) |
| *A61K 31/282* | (2006.01) |
| *A61K 38/38* | (2006.01) |
| *A61K 33/24* | (2019.01) |
| *A61K 31/704* | (2006.01) |
| *A61K 31/337* | (2006.01) |
| *A61N 5/02* | (2006.01) |
| *A61N 1/20* | (2006.01) |
| *A61N 5/00* | (2006.01) |
| *A61M 25/09* | (2006.01) |
| *A61B 1/04* | (2006.01) |
| *A61B 1/06* | (2006.01) |
| *A61N 1/05* | (2006.01) |
| *A61M 25/06* | (2006.01) |
| *A61M 31/00* | (2006.01) |
| *A61M 37/00* | (2006.01) |
| *A61B 90/00* | (2016.01) |
| *A61N 1/32* | (2006.01) |
| *A61B 1/015* | (2006.01) |
| *A61B 5/00* | (2006.01) |
| *A61B 18/00* | (2006.01) |
| *A61B 10/02* | (2006.01) |
| *A61B 6/12* | (2006.01) |
| *A61B 8/08* | (2006.01) |
| *A61B 5/055* | (2006.01) |

(52) U.S. Cl.
CPC .......... *A61M 25/06* (2013.01); *A61M 25/09* (2013.01); *A61M 31/00* (2013.01); *A61M 31/002* (2013.01); *A61M 31/007* (2013.01); *A61M 37/0092* (2013.01); *A61N 1/05* (2013.01); *A61N 1/20* (2013.01); *A61N 5/00* (2013.01); *A61N 5/02* (2013.01); *A61N 5/1001* (2013.01); *A61N 5/1027* (2013.01); *A61B 1/015* (2013.01); *A61B 5/055* (2013.01); *A61B 5/4839* (2013.01); *A61B 6/12* (2013.01); *A61B 8/085* (2013.01); *A61B 10/0233* (2013.01); *A61B 90/361* (2016.02); *A61B 2017/3445* (2013.01); *A61B 2018/00005* (2013.01); *A61B 2018/00273* (2013.01); *A61B 2018/00601* (2013.01); *A61B 2018/00613* (2013.01); *A61B 2018/00982* (2013.01); *A61B 2018/00994* (2013.01); *A61B 2090/3908* (2016.02); *A61B 2090/3987* (2016.02); *A61M 2025/0166* (2013.01); *A61M 2025/09125* (2013.01); *A61M 2025/09141* (2013.01); *A61M 2025/09166* (2013.01); *A61M 2025/09175* (2013.01); *A61N 1/327* (2013.01)

(56) References Cited

U.S. PATENT DOCUMENTS

| | | | |
|---|---|---|---|
| 6,205,352 B1 | 3/2001 | Carroll | |
| 6,306,132 B1 | 10/2001 | Moorman et al. | |
| 6,575,991 B1 | 6/2003 | Chesbrough et al. | |
| 7,077,842 B1* | 7/2006 | Cosman | A61B 18/148 |
| | | | 128/898 |
| 8,052,708 B2 | 11/2011 | Chesbrough et al. | |
| 8,409,111 B2 | 4/2013 | Field et al. | |
| 2002/0143302 A1 | 10/2002 | Hinchliffe et al. | |
| 2004/0073107 A1 | 4/2004 | Sioshansi et al. | |
| 2005/0080410 A1 | 4/2005 | Rioux et al. | |
| 2005/0165288 A1* | 7/2005 | Rioux | A61B 5/0084 |
| | | | 600/342 |
| 2007/0021803 A1* | 1/2007 | Deem | A61N 1/0412 |
| | | | 607/46 |
| 2009/0171293 A1 | 7/2009 | Yang et al. | |
| 2010/0179530 A1* | 7/2010 | Long | A61B 18/1206 |
| | | | 606/33 |
| 2010/0234726 A1 | 9/2010 | Sirimanne et al. | |
| 2010/0261994 A1* | 10/2010 | Davalos | A61B 18/1477 |
| | | | 600/411 |
| 2010/0268029 A1 | 10/2010 | Phan et al. | |
| 2012/0083646 A1* | 4/2012 | Benson | A61N 5/1015 |
| | | | 600/3 |
| 2013/0338467 A1* | 12/2013 | Grasse | A61B 5/042 |
| | | | 600/373 |
| 2014/0214005 A1 | 7/2014 | Belson | |

FOREIGN PATENT DOCUMENTS

| | | |
|---|---|---|
| WO | WO 02/36017 | 5/2002 |
| WO | WO 2004/045480 | 6/2004 |
| WO | WO 2004/088233 | 10/2004 |
| WO | WO 2006/102471 | 9/2006 |
| WO | WO 2008/020967 | 2/2008 |

OTHER PUBLICATIONS

Lee, N.K. et al. "CT-Guided Percutaneoous Transthoracic Localization of Pulmonary Nodules Prior to Video-Assisted Thoracoscopic Surgery Using Barium Suspension", Korean Journal Radiology, 2012; 13(6), pp. 694-701.

* cited by examiner

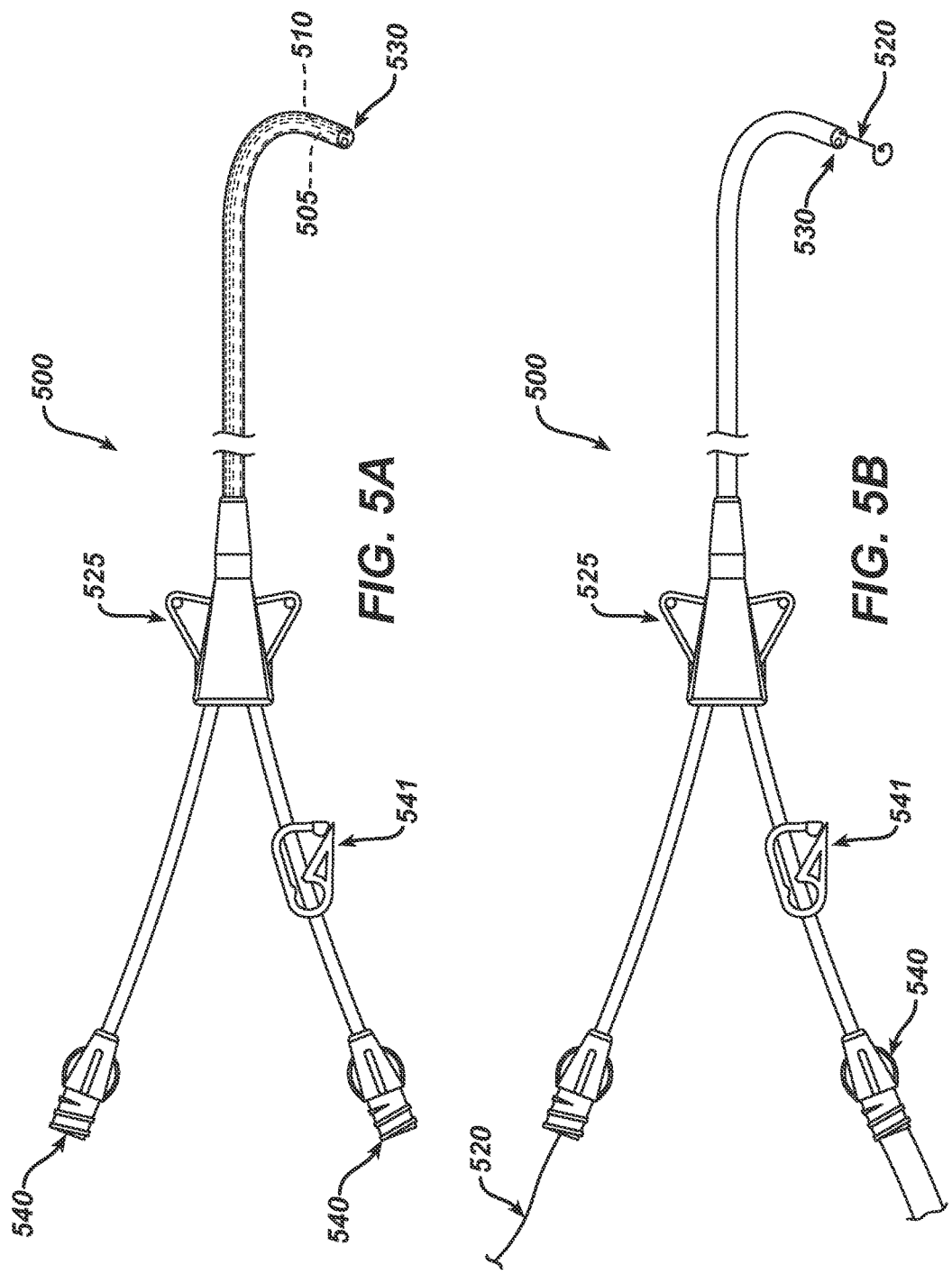

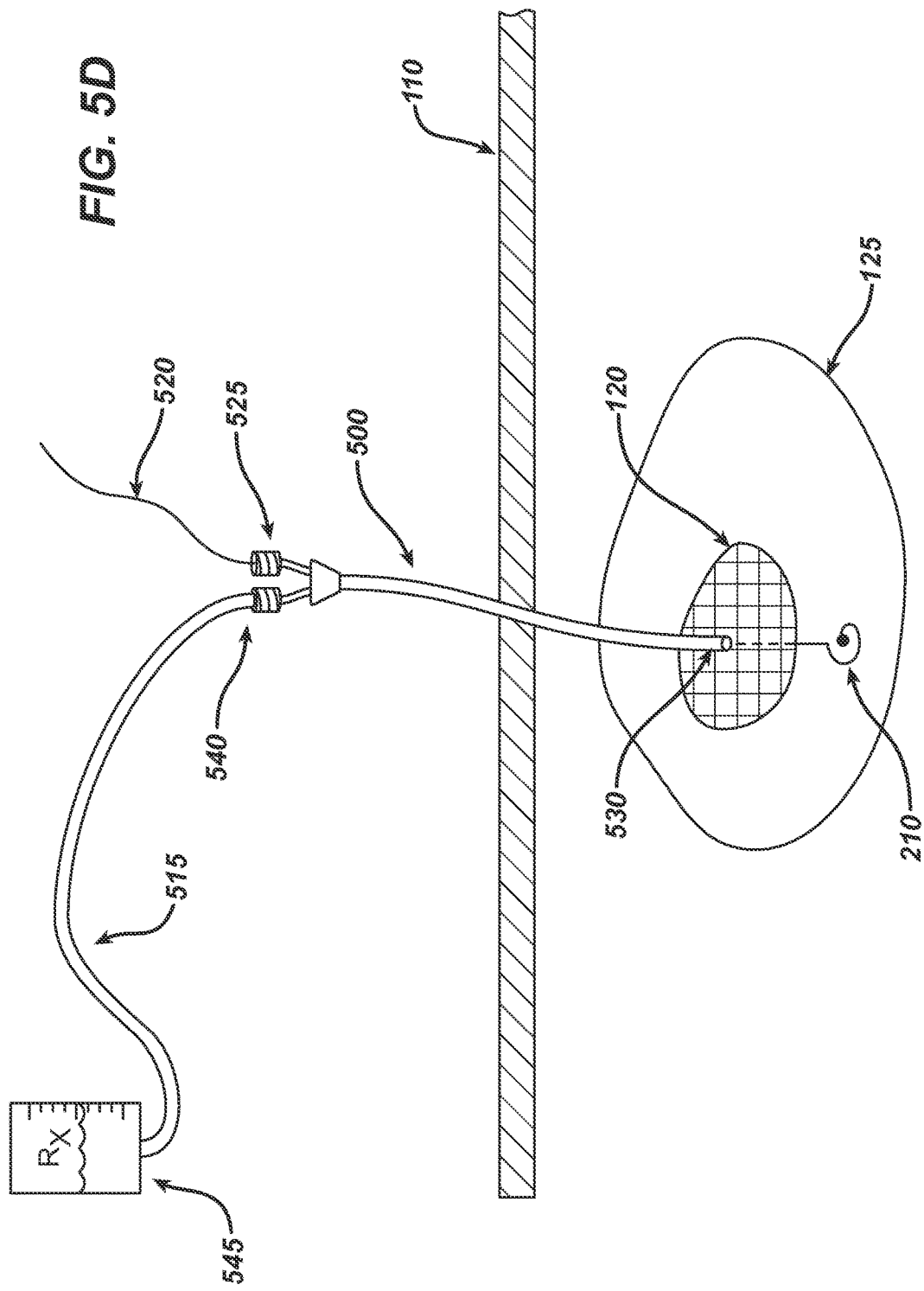

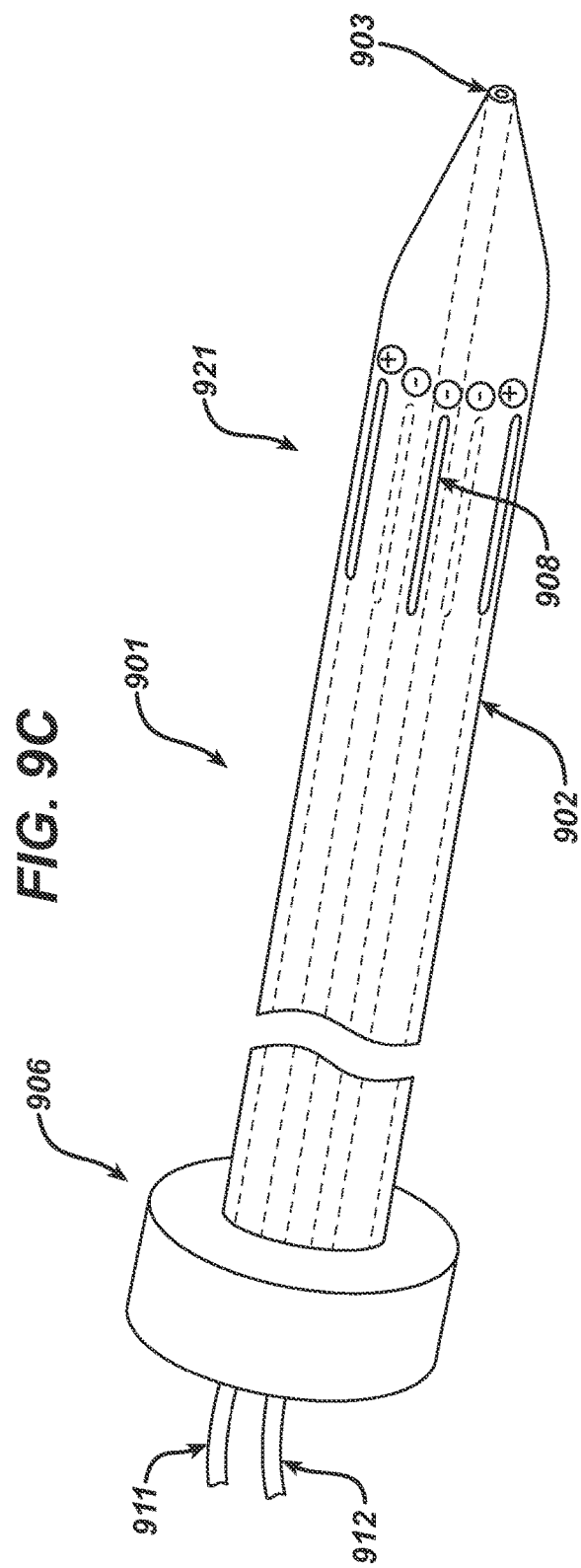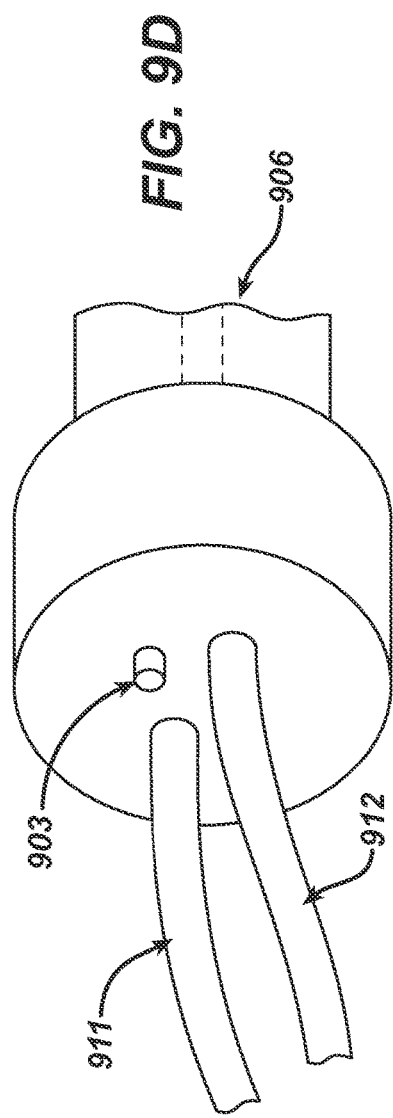

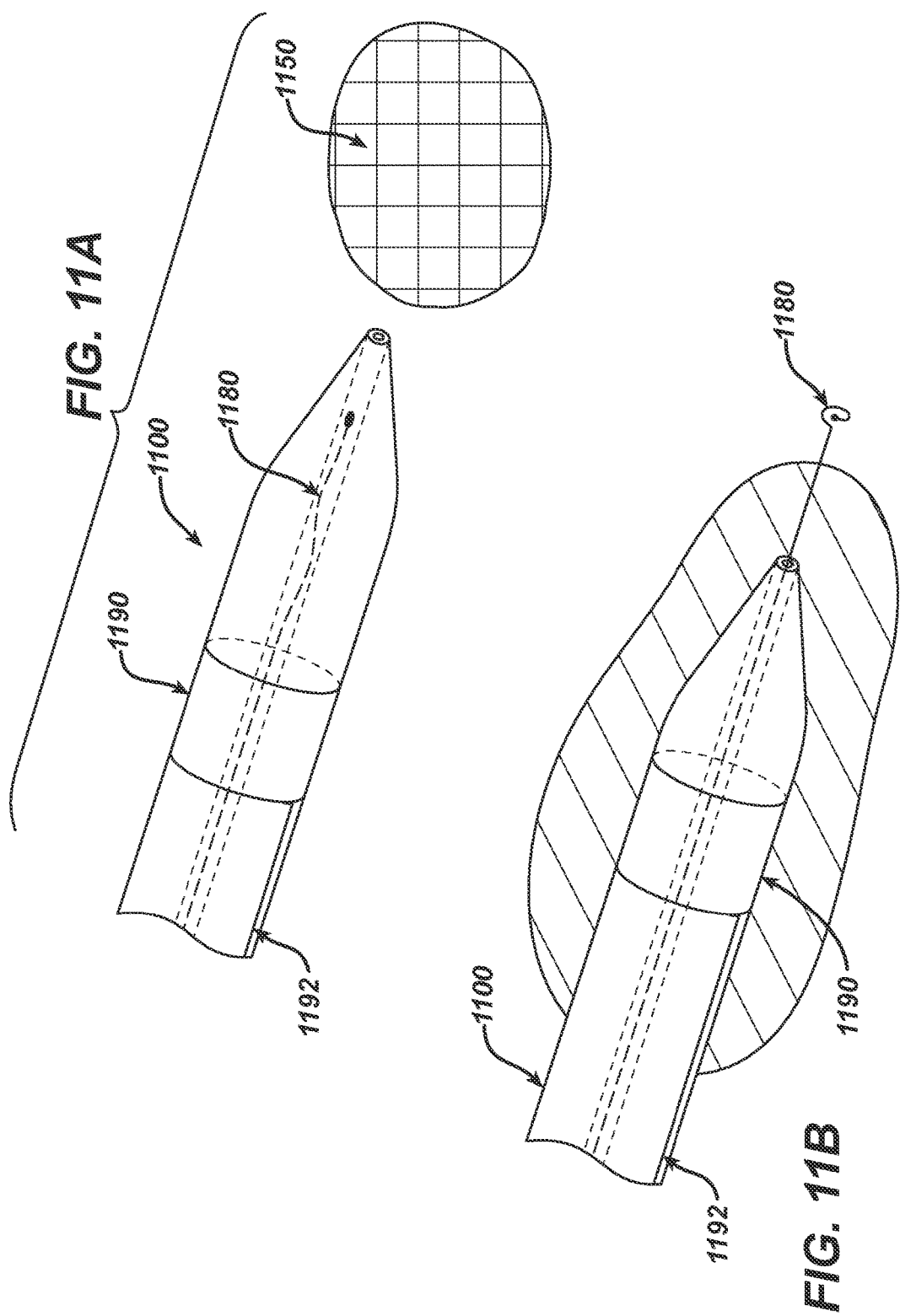

SYSTEM AND METHOD FOR TARGETED DELIVERY OF THERAPEUTIC AGENTS TO TISSUE

FIELD OF THE INVENTION

The field of art to which this invention pertains is medical devices and methods for delivering therapeutic agents, more particularly interventional oncology relating to systems and methods for delivering therapeutic agents to target tissues such as tumors.

BACKGROUND OF THE INVENTION

One dilemma associated with both medical and surgical oncology is the need to delay delivery of adjuvant therapy such as chemotherapeutic agents or radiation to a patient following cytoreductive or excisional surgery to remove malignant tissue. It is believed that the delay will allow the patient to recover from surgery prior to delivering the adjuvant therapy, and to allow for the healing of anastomoses, resections, fascia and skin to occur without the presence of cytotoxic agents. The consequence of this practice is the potential for any residual cancer cells present at the operative site, or sites distant from the operative site, to reproduce and metastasize. As a result, the intended benefits of the surgery may be compromised. Another dilemma associated with both interventional oncology is the need to deliver neoadjuvant therapy, i.e., chemotherapy or radiation prior to surgery, without causing excessive destruction of tissue or toxicity that may affect the patient during surgery or healing post-operatively. Since neoadjuvant therapy is typically stopped 1-2 weeks prior to surgery, the tumor has a chance to grow, thus potentially compromising the intent and benefit of the therapy itself.

Still yet another dilemma associated with surgical and medical oncology are the effects of both neoadjuvant and adjuvant therapeutic agents on normal tissue. The significant side effects associated with chemotherapy may limit its potential effectiveness and in some cases, cause the patient to decline the therapy in favor of palliative care instead.

Still yet another dilemma facing both medical and surgical oncologists is the matter of "inoperable disease". In such a circumstance, tumors may have spread to sites distant from the primary tissue and there may be too many tumors to make surgery feasible. Other "inoperable" tissues may be integrated into or surround vital structures such as an aorta, nerve, or vena cava. Tumors of the pancreas also present challenging issues to surgeons because the tumors invade or abut many vital ducts, vessels, and other structures. In some cases the tumor may be very close to the major blood vessels and it may be difficult for the surgeons to determine with a reasonable degree of certainty whether it is safe enough to take out the cancer solely on the basis of a review of scans of the site. This may require the additional step of beginning the operation with a laparoscopic procedure to make sure it is possible to safely remove the cancer before proceeding on to the full surgery. In other cases surgeons may prescribe a course of chemotherapy or chemo-radiotherapy before surgery to try to shrink the cancer to make it operable. Nonetheless, even with these approaches the prognosis for surviving pancreatic cancer is remarkably grim. Pancreatic cancer (PaCa) is the fourth leading cause of cancer-related death in the United States. The median size of pancreatic adenocarcinoma at the time of diagnosis is about 31 mm and has not changed significantly in last three decades despite major advances in imaging technology that can help diagnose increasingly smaller tumors. This is largely because patients are asymptomatic until late in course of pancreatic cancer or have nonspecific symptoms. Increased awareness of pancreatic cancer amongst the clinicians and knowledge of the available imaging modalities and their optimal use in evaluation of patients suspected to have pancreatic cancer can potentially help in diagnosing more early stage tumors. Another major challenge in the management of patients with pancreatic cancer involves reliable determination of resectability. Only about 10% of pancreatic adenocarcinomas are resectable at the time of diagnosis and would potentially benefit from a surgical resection. The final determination of resectability cannot be made until late during surgical resection. Failure to identify an unresectable tumor pre-operatively can result in considerable morbidity and mortality due to an unnecessary surgery.

The ability to successfully treat patients with cancer is dependent upon the ability to locate a tumor via imaging and subsequent treatment by neoadjuvant therapy, surgery, adjuvant therapy, or combinations thereof. In some instances, imaging modalities such as computed tomography (CT) or magnetic resonance imaging (MRI) may detect small tumors that are undetectable by palpation, gross observation or endoscopic visualization. Localization techniques for small or inoperable tissues can be classified into three major types: image-guided surgery; injection of liquid materials through fine needles; and, placement of percutaneous wires.

For example, the use of ultrasonography (US)—guided surgery in lung cancer surgery may be time-consuming in the operating room because the lung parenchyma must be completely deflated for visualization, and this may be impossible in patients with extensive emphysema. In addition, growing nodules are most commonly identified with CT, and it may be difficult to ascertain with certainty that the nodule identified at intraoperative US is the growing nodule seen on the preoperative CT scan. Guidance with use of liquid materials, including methylene blue dye, contrast medium, and radionuclides, has also been evaluated. However, liquids may diffuse away from the nodule such that fixed time intervals between localization and surgical resection are required. There is also a potential risk of systemic embolization if the solutions are inadvertently injected into the pulmonary venous system.

Localizing wires are well-known devices for marking areas, such as tissues, in a tissue mass, frequently breast tissue. When such a tissue is identified with a medical imaging technique, such as radiography or ultrasonography, it is often desirable to position a localizing wire or other type of imaging marker near the tissue to facilitate locating the tissue during later procedures, such as biopsy or surgery. A practitioner can then use the wire as a visual and tactile guide to the tissue rather than solely relying on imaging techniques, which currently provide good 2-D images but not 3-D images. During surgery, surgeons typically prefer a localizing wire to locate the tissue because it leads them straight to the biopsy site. The implantation of a localizing wire requires a needle to be inserted into the tissue mass under guidance from an imaging system. The needle is positioned with its tip at a selected location at or near the tissue. Once the needle is in place, the localizing wire is extended through the needle and out the tip into or adjacent the tissue where the hook on the end of the wire engages the tissue mass. Thereafter, the needle is removed from the tissue mass, and the localizing wire remains in the tissue.

While the known tumor localization systems described above are sufficiently able to direct the surgeon to a target tissue, they are limited to that function and lack the capability of delivering neoadjuvant or neoadjuvant therapy directly to the tumor or adjacent tissue. Furthermore, if the cancer has been present long enough such that some of the cancer is outside of the field of surgical removal, recurrence is inevitable no matter how thorough or complete the surgery. There is a need in this area, and it would be beneficial to cancer patients, for medical devices and methods of treatment that provide for the administration of chemotherapy, radiation, electroporation, or RF energy, etc., which could be enabled at periods of time that most favorably impact the course of the disease, and have the delivery of these agents focused on the tumor or surrounding tissue without having to deliver the agents systemically. It would further aid both patients and clinicians, and advance the standard of care, if rapid and repeated multi-modal treatments of the tumor can be made without the need for subsequent imaging.

SUMMARY OF THE INVENTION

Accordingly, a novel method and system for delivering therapeutic agents to target tissue sites such as a tumor is disclosed herein. The method of delivering a therapeutic agent to a target tissue involves the steps of identifying a target tissue via an imaging modality and then placing the distal end of a needle proximate the target tissue. A guidewire is then advanced in the lumen of the needle so that the distal end of the guidewire is positioned proximate the target tissue. The distal end of the guidewire has anchoring means that enable it to be securely attached to tissue. The needle is then removed from the patient. A cannula having a proximal end and a distal end and at least two lumens is then advanced, by using one of the cannula lumens, over the guidewire towards the target tissue. The distal end of the cannula is then positioned proximate the target tissue. One lumen of the cannula is then coupled to a source of therapeutic agent which is then delivered to the target tissue. The therapeutic agents may include, for example, an energy source, a chemotherapeutic agent, etc.

Another aspect of the present invention is a system for delivering a therapeutic agent to a target tissue. The system has a needle having a distal end and a proximal end, and a lumen that communicates between the proximal and distal ends. It additionally has a guidewire with proximal and distal ends, the guidewire having a diameter less than the diameter of the needle lumen. The guidewire has anchoring means on its distal end. The system also has a cannula having two or more lumens; at least one of the lumens has a diameter greater than the diameter of the guidewire. The system also has a source of therapeutic agent such as energy or chemotherapeutic agent.

Yet another aspect of the present invention is a method of treating tumor cells in lymphatic tissue and the lymphatic system utilizing the novel systems of the present invention.

These and other aspects and advantages of the present invention will become more apparent from the following description and accompanying drawings.

BRIEF DESCRIPTION OF THE DRAWINGS

FIG. 5A illustrates a cannula of the system of the present invention having a guidewire lumen and a therapeutic agent lumen;

FIG. 5 B illustrates the cannula of FIG. 5B with a source of therapeutic agent attached and a guidewire placed through the cannula;

FIGS. 9A-D are partial perspective views illustrating an alternate embodiment of a system of the present invention having a cannula with a lumen for a guidewire and electrodes for electroporation or bipolar RF ablation.

FIGS. 11A-B are partial perspective views of a monopolar configuration of electrodes on a cannula for use in RF ablation or electroporation in the systems of the present invention; a target tissue is shown in cross-section.

DETAILED DESCRIPTION OF THE INVENTION

Figure 1:
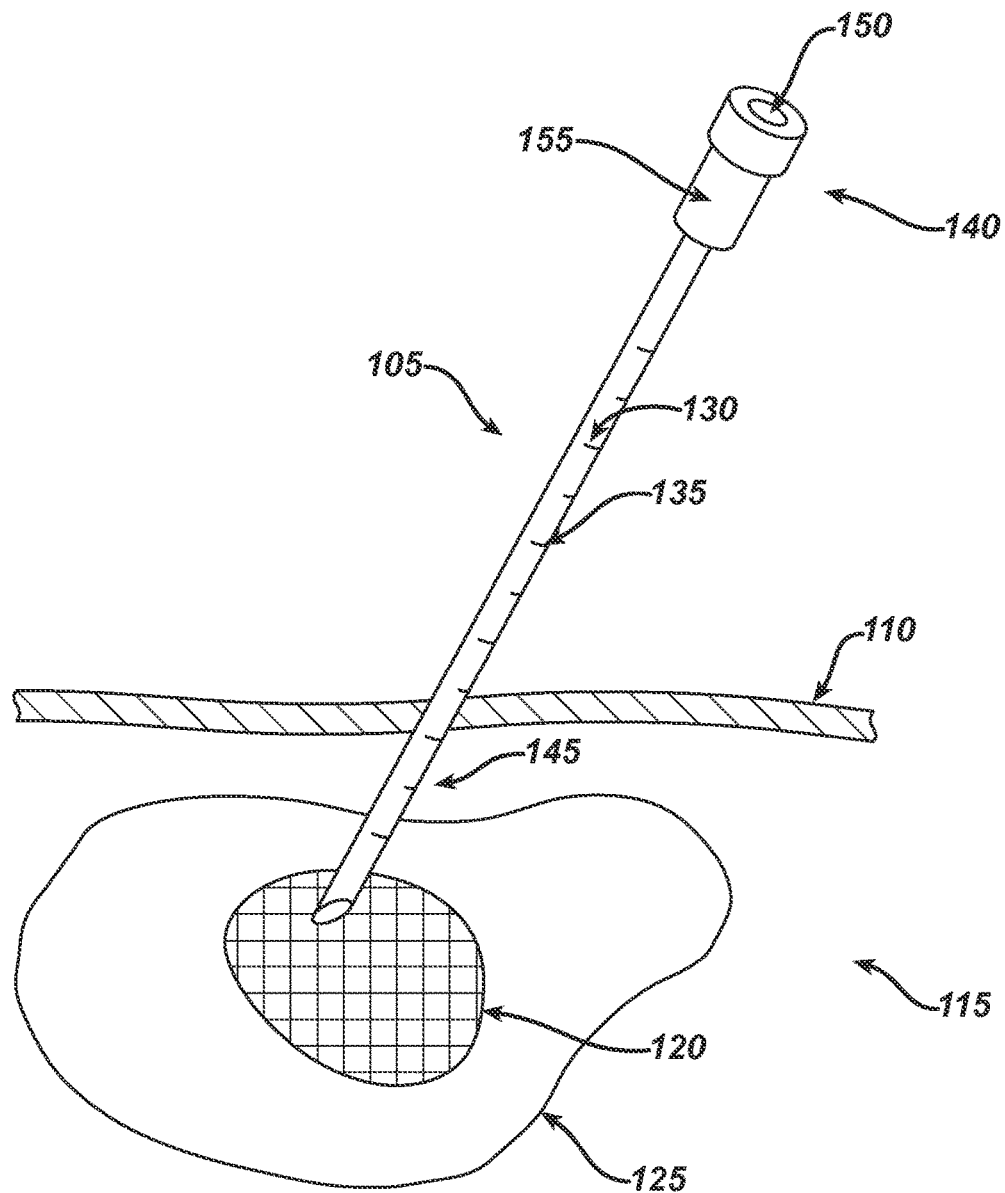
FIG. 1 is an illustration of a needle of the system of the present invention being passed through a body wall and into a target tissue such as a tumor; the body wall and tumor are shown in cross-section.

The inventions described herein include a novel method and a system to deliver therapeutic agents to a target tissue. The term target tissue as used herein is defined to mean any tissue known or suspected of having benign, pre-cancerous, or malignant tumor cells within it. The method is comprised of the steps of initially identifying a target tissue via a conventional imaging modality, such as computer tomography or magnetic resonance imaging or direct or indirect visualization, inserting a needle proximate the target tissue; inserting a guidewire through the lumen of the needle and advancing it so that the distal end of the guidewire is positioned proximate the target tissue; removing the needle from the patient; advancing a cannula over the guidewire so as to place the distal end of the guidewire proximate the target tissue; coupling the cannula to a source of therapeutic agent such as energy or a reservoir of chemotherapeutic agent; and, delivering energy or a chemotherapeutic agent from or through the distal end of the cannula. For the purposes of this disclosure, the term proximate means within the target tissue or within a sufficiently effective distance thereof, e.g., 5 cm of any edge of the target tissue. Conventional imaging modalities and their equivalents such as computerized tomography, magnetic resonance imaging, positron emission tomography, fluorography, ultrasound, radioimmunoscintigraphy, direct visualization during open surgery or direct endoscopic visualization, or radiography are all useful for this method. The novel systems and methods of the present invention can be used to treat a number of disease states including cancer.

In one embodiment, the system is used to treat solid tumors involving the bile duct, bile duct, breast, pancreas, cervix, endometrium, lung, prostate or rectum. The system is comprised of a needle to penetrate tissue, the needle having a lumen, a guidewire capable of being advanced through the lumen and having anchoring means on its distal end, a cannula having two or more lumens, at least one of which is capable of being slidably engaged with the guidewire, and a source of conventional therapeutic agent such as energy or chemotherapeutic agent. By way of example and not limitation, suitable chemotherapeutic agents are Bortezomib (Velcade); platinums such as cisplatin (Platinol), oxaliplatin (Eloxatin), and carboplatin (Paraplatin); taxanes such as docetaxel (Docefrez or Toxotere), paclitaxel (Taxol), and thalidomide (Synovir or Thalomid); and vinca alkaloids such as vincristine (Vicasar), vinorelbine (Navelbine), and vinblastine (Velban). Other chemotherapeutic agents may also be used alone or in concert with other therapeutic agents, depending on the tumor type, stage, and grade. Patient comorbidities and the toxicity of the agents used may also influence the types and doses of the agents selected, In one embodiment, the therapeutic agent is selected from chemotherapeutic agents, biological agents such as a vascular endothelial cell growth factor (VEGF) inhibitor or monoclonal antibody, or a cocktail of at least two therapeutic agents and equivalents thereof. Biological therapy involves the use of living organisms, substances derived from living organisms, or laboratory-produced versions of such substances to treat disease. Some biological therapies for cancer use vaccines or bacteria to stimulate the body's immune system to act against cancer cells. These types of biological therapy, which are sometimes referred to collectively as "immunotherapy" or "biological response modifier therapy," do not target cancer cells directly. Other biological therapies, such as antibodies or segments of genetic material (RNA or DNA), do target cancer cells directly. Biological therapies that interfere with specific molecules involved in tumor growth and progression are also referred to as targeted.

Some monoclonal antibodies (MAbs) stimulate an immune response that destroys cancer cells. Similar to the antibodies produced naturally by B cells, these MAbs "coat" the cancer cell surface, triggering its destruction by the immune system. Monoclonal antibodies of this type include rituximab, which targets the CD20 antigen found on non-Hodgkin lymphoma cells, and alemtuzumab, which targets the CD52 antigen found on B-cell chronic lymphocytic leukemia (CLL) cells. Another group of MAbs stimulates an anticancer immune response by binding to receptors on the surface of immune cells and inhibiting signals that prevent immune cells from attacking the body's own tissues, including cancer cells. One such MAb, ipilimumab, is used to treat metastatic melanoma. Other MAbs interfere with the action of proteins that are necessary for tumor growth. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels.

Similarly, cetuximab and panitumumab target the epidermal growth factor receptor (EGFR), and trastzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

Another group of cancer therapeutic MAbs are the immunoconjugates. These MAbs, which are sometimes called immunotoxins or antibody-drug conjugates, consist of an antibody attached to a cell-killing substance, such as a plant or bacterial toxin, a chemotherapy drug, or a radioactive molecule. The antibody latches onto its specific antigen on the surface of a cancer cell, and the cell-killing substance is taken up by the cell. FDA-approved conjugated MAbs that work this way include $^{90}$Y-ibritumomab, which targets the CD20 antigen to deliver radioactive yttrium-90 to B-cell non-Hodgkin lymphoma cells; $^{131}$I-tositumomab, which targets the CD20 antigen to deliver radioactive iodine-131 to non-Hodgkin lymphoma cells; and ado-trastuzumab emtansine, which targets the HER-2 molecule to deliver the drug DM1, which inhibits cell proliferation, to HER-2 expressing metastatic breast cancer cells.

Another biological agent that may be used as a therapeutic agent in this system is a cytokine Cytokines are signaling proteins that are produced by white blood cells. Two types of cytokines are used to treat patients with cancer: interferons and interleukins. A third type, called hematopoetic growth factor, is used to counteract some of the side effects of certain chemotherapy agents.

In one embodiment, the therapeutic agent is a vaccine. Cancer treatment vaccines are designed to treat cancers that have already developed rather than to prevent them in the first place. Cancer treatment vaccines contain cancer-associated antigens to enhance the immune system's response to a patient's tumor cells. The cancer-associated antigens can be proteins or another type of molecule found on the surface of or inside cancer cells that can stimulate B cells or killer T cells to attack them.

In one embodiment, the therapeutic agent is an oncolytic virus. Oncolytic virus therapy is an experimental form of biological therapy that involves the direct destruction of cancer cells. Oncolytic viruses infect both cancer and normal cells, but they have little effect on normal cells. In contrast, they readily replicate, or reproduce, inside cancer cells and ultimately cause the cancer cells to die. Some viruses, such as reovirus, Newcastle disease virus, and mumps virus, are naturally oncolytic, whereas others, including measles virus, adenovirus, and vaccinia virus, can be adapted or modified to replicate efficiently only in cancer cells. In addition, oncolytic viruses can be genetically engineered to preferentially infect and replicate in cancer cells that produce a specific cancer-associated antigen such as EGFR or HER-2.

In one embodiment, the therapeutic agent is a genetic material such as RNA or DNA. Researchers are studying several methods for treating cancer with gene therapy. Some approaches target cancer cells, to destroy them or prevent their growth. Others target healthy cells to enhance their ability to fight cancer. In some cases, researchers remove cells from the patient, treat the cells with the vector in the laboratory, and return the cells to the patient. In others, the vector is given directly to the patient.

In one embodiment, the therapeutic agent is a heated fluid such as heated physiologic saline. This heated fluid enables hyperthermia to occur and can shrink tumors by using heat to damage proteins and structures within cancer cells. Hyperthermia (also called thermal therapy or thermotherapy) is a type of cancer treatment in which body tissue is exposed to temperatures of 40-45 degrees Celsius. Local hyperthermia (sometimes called superficial hyperthermia) exposes a small area, such as a tumor, to high temperatures. Hyperthermia can be used with radiation therapy, chemotherapy and immunotherapy. In an alternative embodiment, the therapeutic agent is a cryotherapeutic agent such as liquid nitrogen or compressed argon gas. Exposing the target tissue to temperatures near or less than minus 20 degrees Celsius for periods of 1 minute or longer is a known method to ablate or kill tissue, including the tumor cells. The system can also be used to deliver other therapeutic agents such as antimicrobial agents, antibiotics, anti-inflammatory agents such as steroids or NSAIDS, analgesics, opiates, anesthetics, vascular endothelial cell growth factor inhibitors, growth factors, dyes, radiosensitizers, or drug that targets genetic defects in tumor cells, such as Tarceva.

In one embodiment, the system is used to deliver a therapeutic agent such as radiation by facilitating the placement of conventional radioactive elements proximate the target tissue, e.g., a tumor. The system can also be used to deliver a therapeutic agent such as RF energy to ablate tissue. In one embodiment, the system is used to enable reversible electroporation. In one embodiment, the system is used to enable irreversible electroporation. The system may also be used in conjunction with other cancer treatments, such as radiation therapy, surgery, or hyperthermia. This is accomplished by leaving the guidewires in the target tissue and switching from one cannula designed to deliver chemotherapeutic agents over a guidewire to another cannula designed to deliver brachytherapy implants over a guidewire, to a target tissue.

Referring to FIG. 1, a needle 105 useful in the systems and methods of the present invention is shown penetrating the wall 110 of a body cavity 115 and directed, preferably under radiographic imaging such as computed tomography (CT) or fluoroscopic guidance, towards a target tissue 120 that exists in an organ 125. The needle 105 has a proximal end 140, a distal end 145, and a lumen 150 that communicates between both ends. The proximal end 140 of the needle 105 is seen to have a hub 155 for connecting to a source of therapeutic agent. In one embodiment, this hub is a male or female luer-lock type connection. Other conventional guidance systems such as ultrasound or MRI may also be used to place the needle 105. The needle can be placed percutaneously or directly into a target tissue during open or minimally invasive surgery. The needle 105 is preferably 18-22 gauge and 5-20 cm long, although other diameters and lengths may be used. To provide strength to the needle 105 so as to prevent bending, the needle 105 may have an optional core or stylet in lumen 150 (not shown), such as a 10 cm or 15 cm long Chiba needle (Cook Canada, Stouffville, Ontario, Canada). The optional core can be removed once the needle 105 is in place within the target tissue 120, e.g., a tumor. In one embodiment, the needle 105 has a plurality of equally spaced markings 130 on the outside surface of the needle shaft 135 to indicate depth of penetration.

Figure 2:
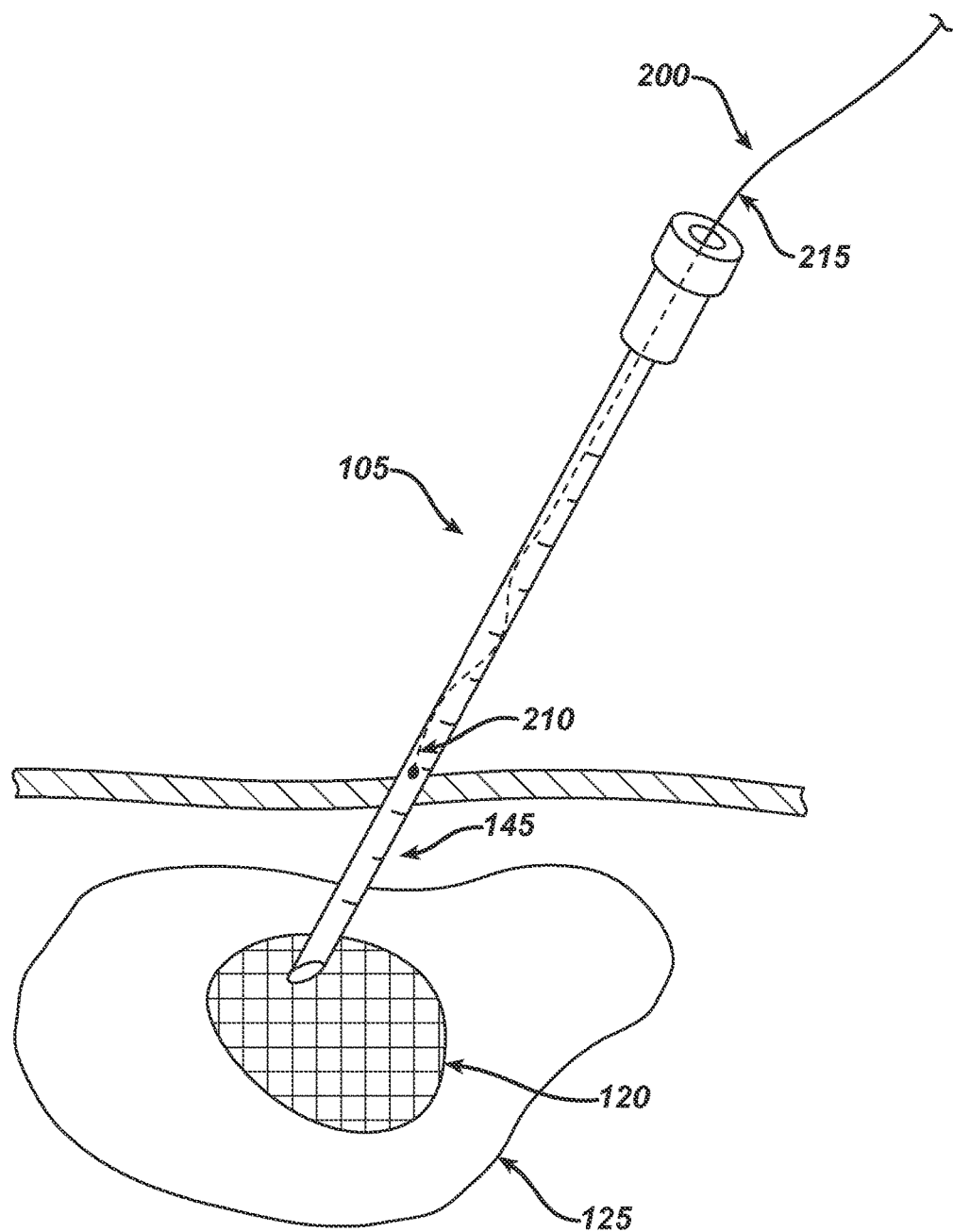
FIG. 2 is an illustration of a guidewire being passed through the lumen of the needle of FIG. 1 toward the distal end of the needle, which has been placed near the target tissue.

Once placement of the needle 105 is confirmed to be proximate or within the target tissue 120 by image guidance or direct visualization, a guidewire 200 with a distal anchoring portion 210 is then loaded into the needle. The guidewire preferably has a conventional hydrophilic coating to reduce friction with adjacent surfaces such as the inner wall of a cannula. Examples of such coatings may include polyurethane, polyvinylpyrrolidone (PVP), hyaluronic acid, polyvinylalcohol (PVA), silicone, or polyacrylate and, depending on the polymer, these coatings can be cured onto the guidewire surface by heat or UV light. FIG. 2 illustrates a guidewire 200 being passed towards the distal end 145 of needle 105 placed near a target tissue 120 such as a tumor that may be present in an organ 125 such as a pancreas. In one embodiment, the guidewire 200 has an anchoring portion 210 and a non-anchoring portion 215. In FIG. 2, the needle 105 has not passed all of the way through the target tissue 120. In some cases the surgeon may want to pass the needle 105 all of the way through the target tissue 120. The actual placement of the needle 105 relative to the target tissue 120 is thus a decision made by the surgeon or radiologist, and will depend on factors such as proximity to vital structures such as major blood vessels, for example. The guidewire 200 can be made from conventional biocompatible materials such as stainless steel, nitinol, gold, platinum, tantalum, or other metals or alloys or materials known to be suitable for interventional procedures. The diameter of the guidewire will be sufficient to effectively direct a cannula to the target tissue without kinking or breaking yet still be able to be flexible to enable ease of cannula advancement over the guidewire and can, for example, range from 0.05-1.0 mm. In one embodiment, the guidewire 200 is made from nitinol and the non-anchoring portion 215 of the guidewire 200 is 40-cm-long and 0.018-inch in diameter. While in the lumen 150 of the needle 105, the anchoring portion 210 of the guidewire 200 is in a straight or slightly bent configuration. The degree of bending within the lumen 150 of the needle 105 will depend on the amount of space between the guidewire 200 and the inner wall of the needle lumen 150. In one embodiment, the anchoring portion 210 of the guidewire 200 can be welded onto the non-anchoring portion 215 of the guidewire 200. The anchoring portion 210 may or may not be made of the same material as the non-anchoring portion 215 of the guidewire 200. In one embodiment, the anchoring portion 210 of the guidewire 200 is comprised of nitinol and processed so that it assumes a second "shape memory" configuration when released from the needle lumen 150. In one embodiment, either the anchoring portion 210 or the non-anchoring portion 215 are comprised of surgical grade stainless steel.

Figure 3:
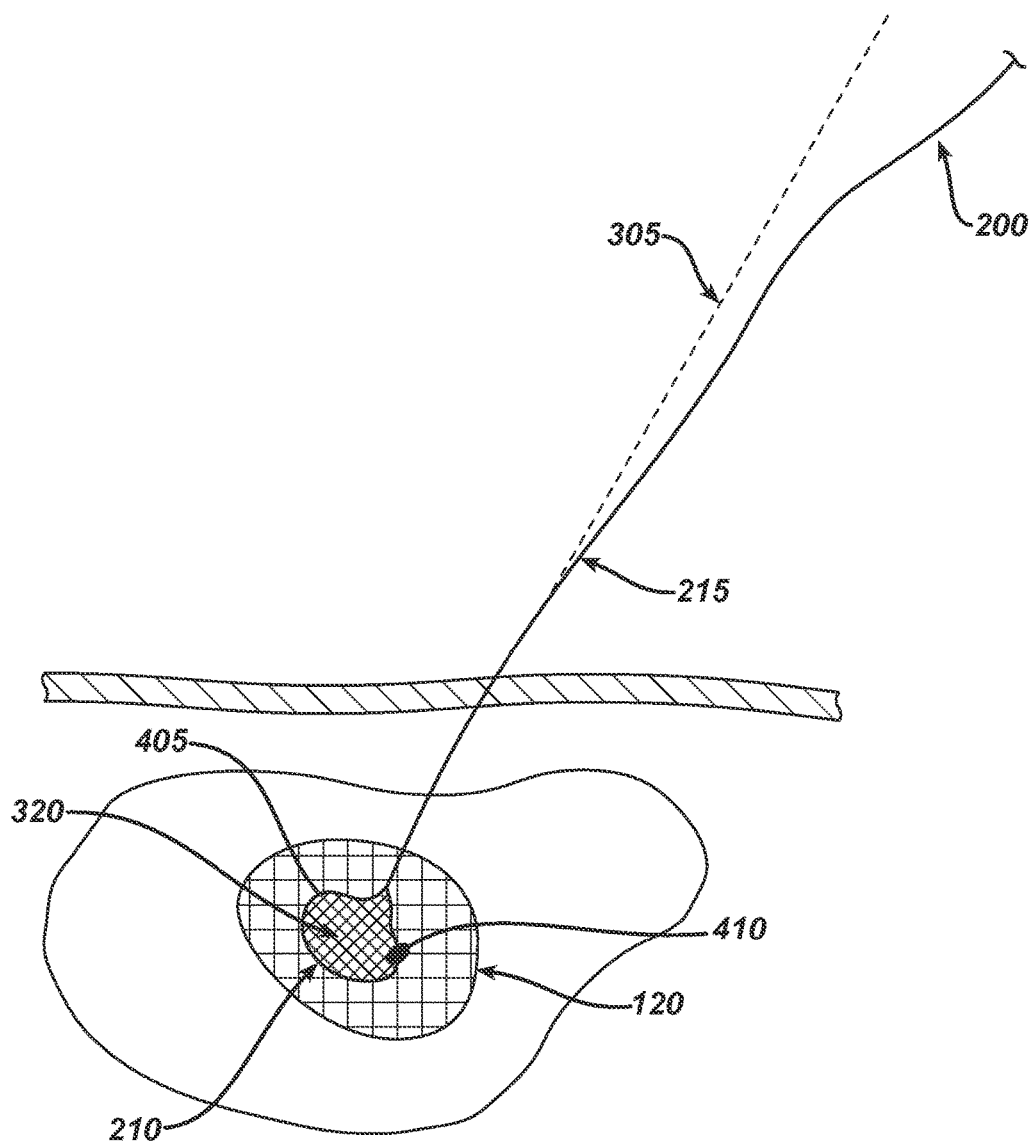
FIG. 3 is an illustration of the guidewire of FIG. 2 anchored into the target tissue after having been passed through the needle.

In one embodiment, the anchoring portion 210 of the guidewire 200 is able to exist in a confined state while in the lumen 150 of the needle 105 and then assume a second configuration when in or proximate the target tissue 120. FIG. 3 illustrates the anchoring portion 210 outside of the needle 105, which has been removed by the surgeon, and within a target tissue 120 such as a tumor. The anchoring portion 210 of the guidewire 200 is in a second configuration, such as a semicircular shape 405, the semi-circle forming a plane 320 that is substantially perpendicular to the axis 305 of the non-anchoring portion 215 of the guidewire 200. In FIG. 3, the needle 105 has been removed from the patient. It is important that the anchoring portion 210 of the guidewire 200 securely engage the tissue proximate or in the target tissue 120 without damaging the tissue. The anchoring portion 210 of the guidewire 200 has an optional atraumatic end 410 in the shape of a ball or bulb shaped end. This atraumatic end 410 will prevent inadvertent passage of the guidewire 200 into non-target tissues. It is also important that the anchoring portion 210 be constructed and configured to be reversibly deployed back into the first configuration by advancing the needle 105 over the guidewire 200 anchoring portion 210 or capable of being removed by itself without damaging tissue.

Figure 4A:
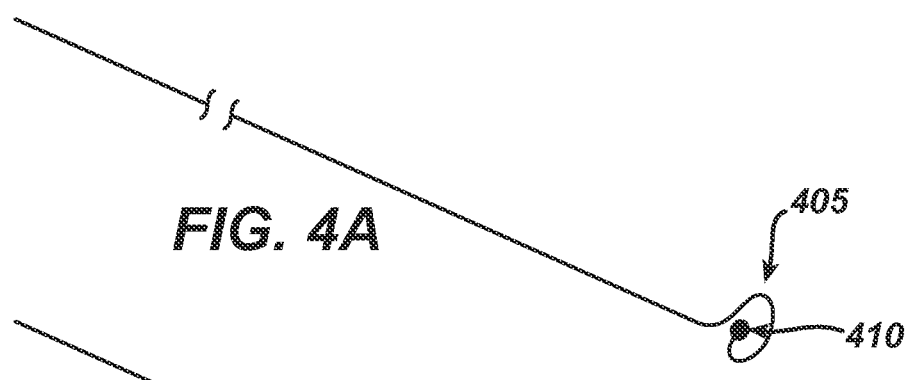
FIGS. 4A-I illustrate various guidewire anchor configurations useful in the systems of the present invention.
Figure 4B:
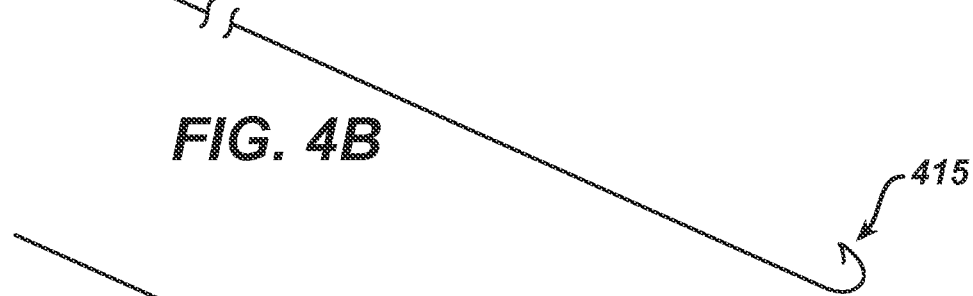
Figure 4C:
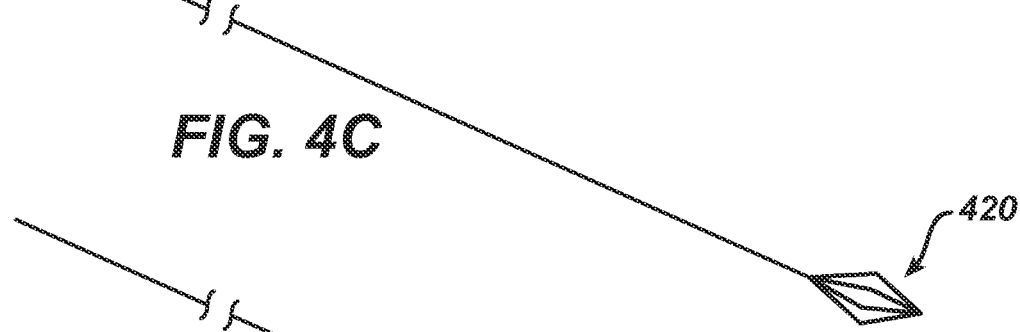
Figure 4D:
Figure 4E:
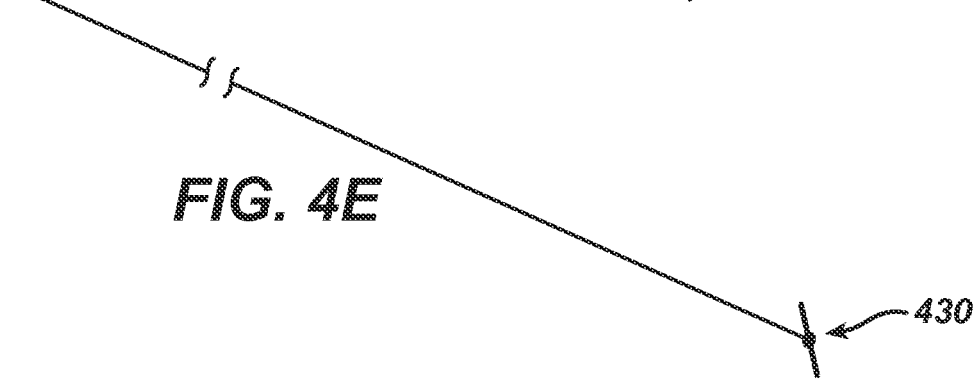
Figure 4F:
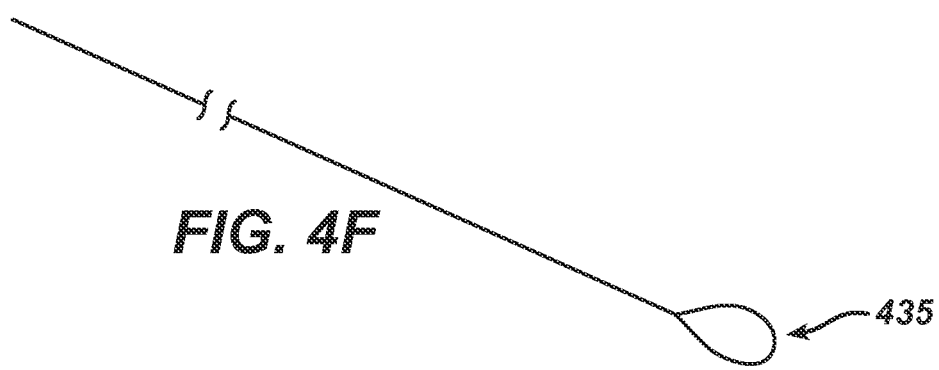
Figure 4G:
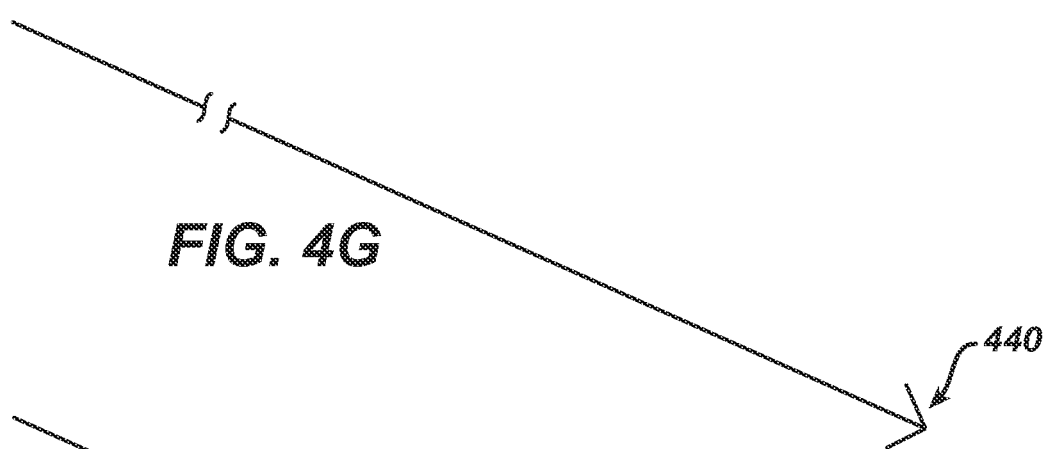
Figure 4H:
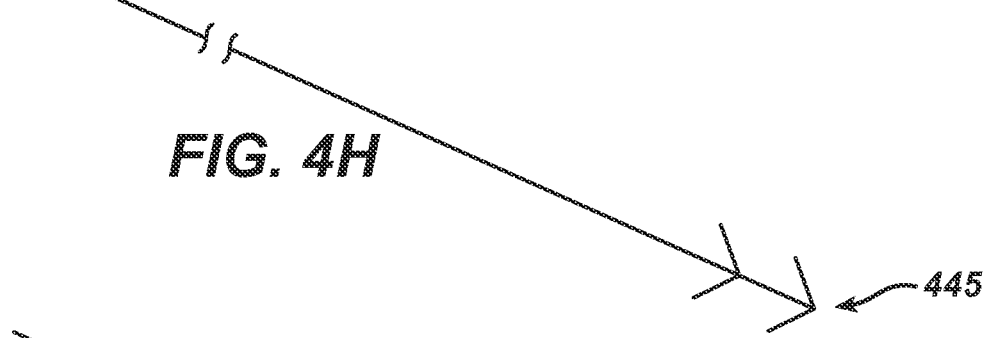
Figure 4I:

Referring to FIGS. 4A-4I, various configurations that the anchoring end 210 of the guidewire 200 may have are illustrated. In one embodiment, the anchoring portion 210 of the guidewire 200 may be comprised of nitinol while the non-anchoring portion 215 of the guidewire is comprised of stainless steel or platinum or tantalum. The configuration may be reversed as well, i.e., the non-anchoring portion 215 of the guidewire 200 is nitinol and the anchoring portion 210 is stainless steel. For example, as seen in FIG. 4A, the anchoring portion 210 may have an open loop that forms a semi-circle 405 having a plane substantially perpendicular to the axis of the non-anchoring portion 215 of the guidewire 200. In one embodiment, the tip of the semi-circular anchor 405 has an atraumatic bulb 410 disposed thereon. Other configurations for the anchoring portion 210 of the guidewire 200 include a hook 415 (FIG. 4B), collapsible polygon 420 (FIG. 4C), harpoon 425 (FIG. 4D), toggle 430 (FIG. 4E), closed loop 435 (FIG. 4F), arrow head 440 (FIG. 4G), barbed arrow 445 (FIG. 4H) or pigtail 446 (FIG. 4I) configuration. In one embodiment, the anchoring portion 210 may have regions that contain conventional radio-opaque markers to facilitate accurate placement of the guidewire in tissue and subsequent imaging of the guidewire 200 location relative to the target tissue 120, if necessary.

Figure 13A:
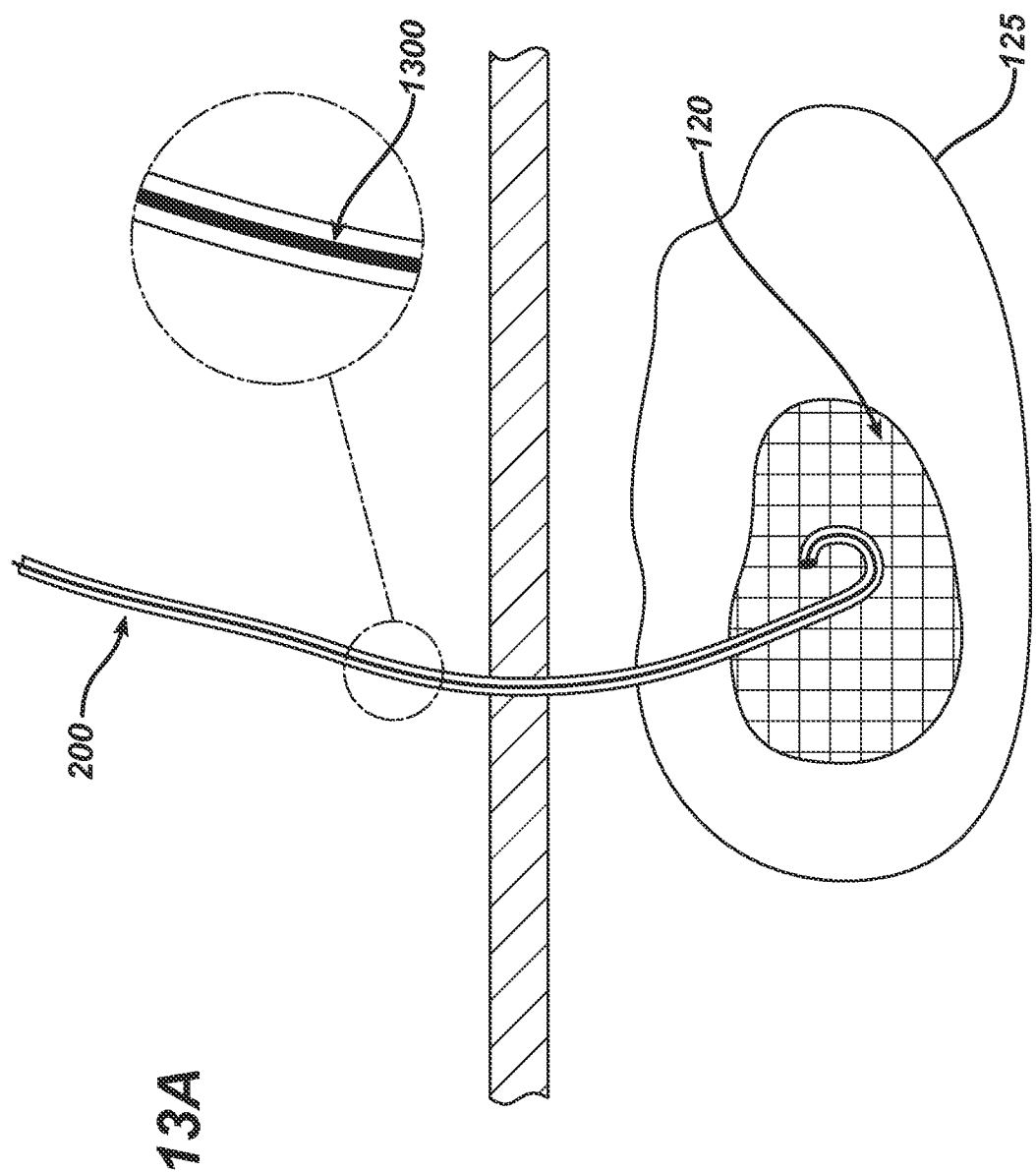
FIGS. 13A-B are illustrations of a guidewire useful in the systems of the present invention having directional and depth markers used to direct surgeon to site of target tissue; a body wall and target tissue are shown in cross-section.
Figure 13B:
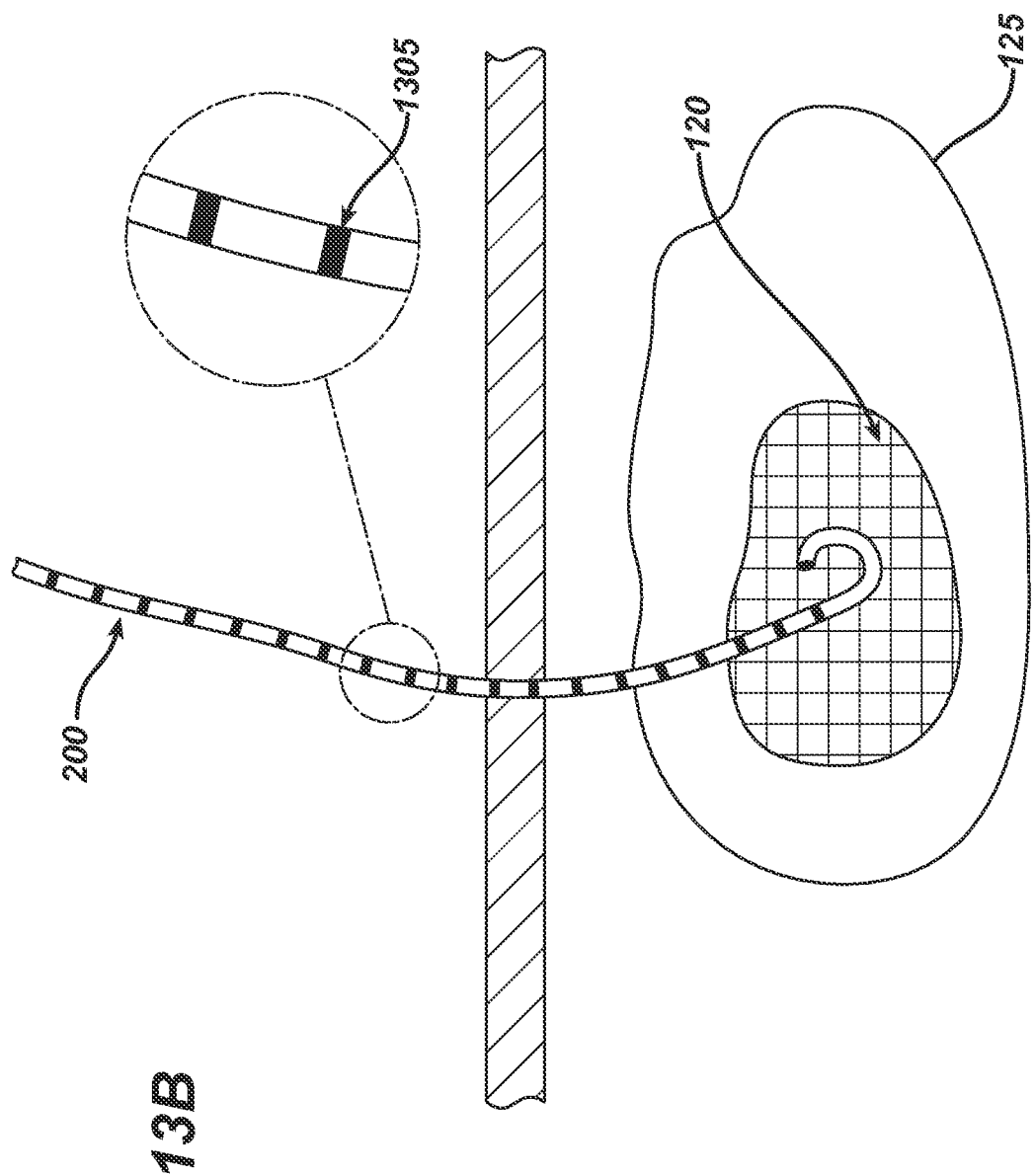

FIG. 13A illustrates an embodiment of the guidewire, in which the guidewire 200 has a directional marker located 1300 on at least one point along its length. The directional marker 1300 may be a colored marking on one side of the guidewire 200 so that when the guidewire 200 is viewed endoscopically, the surgeon can see what direction the target tissue 120 within an organ 125 is located relative to the guidewire 200. The importance of this feature will be described in greater detail below when the therapeutic agent used with the system is radioactive implants or electroporation. In another embodiment illustrated in FIG. 13B, the guidewire 200 has radiopaque bands 1305 located at equally spaced intervals along its length. The bands 1305 are shown as extending completely around the guidewire 200 circumference, but may also extend partially. The bands 1305 can be polymer or metal that are either inherently radiopaque or contain radiopaque substances such as barium, iodine, titanium, tungsten, barium sulfate, and zirconium oxide. The bands 1305 may be spaced at sufficiently effective intervals of, for example, 0.1-1 cm length along the length of the non-anchoring portion 215 of the guidewire to facilitate determination of the spatial positioning of the guidewire, for example, of how deep the target tissue 120 is relative to the surface of the patient's skin. The guidewire is preferably coated with a lubricious coating or fluoropolymer coating to prevent undue friction with the lumen in the cannula.

FIG. 5A illustrates a cannula 500 having a lumen 505 for a therapeutic agent to be delivered to a target tissue and a lumen 510 for a guidewire to be placed there through. The cannula can be made from conventional, biocompatible materials known to be useful in the construction of catheters or cannula and include such polymers as polyetheretherketone (PEEK), polyimides, polyvinylchloride (PVC), polyolefins, fluoropolymers, polyamides, silicone, latex rubber, and polyurethanes, and combinations thereof and equivalents. The cannula 500 is seen to have a proximal end 525 and a distal end 530. The proximal end has an opening 535 for a guidewire and an attachment port 540 for a source of therapeutic agent.

FIG. 5B illustrates a cannula 500 with a tube 515 that is in fluid communication with a source of therapeutic agent (not shown), and, a guidewire 520 placed through the cannula 500. A clamp 541 is present on the tube 515 to allow for control of fluid flow there through.

Figure 5C:
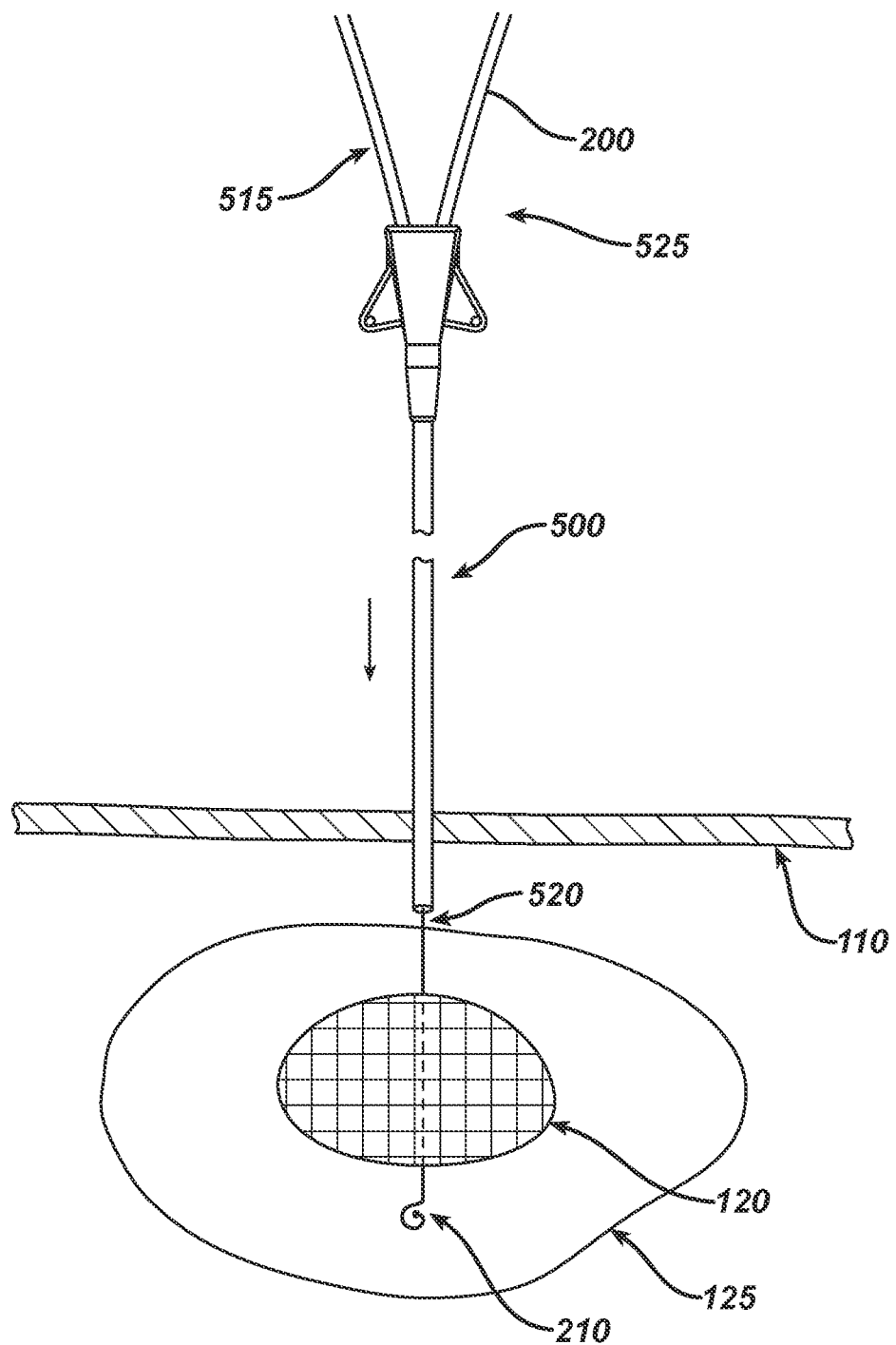
FIG. 5C illustrates the cannula being advanced through a body wall over the guidewire toward a target tissue, wherein the target tissue is a tumor, the body wall and target tissue are shown in cross-section; and, FIG. 5D illustrates a therapeutic agent being delivered through the cannula to the target tissue.

FIG. 5C illustrates a cannula 500 being advanced over the guidewire 520 towards a target tissue 120 such as a tumor within in a patient. The tumor may exist in an organ 125, and in one embodiment, the organ is accessed by going through a body wall 110. In FIG. 5C, the anchoring portion 210 of the guidewire 520 has been passed through the target tissue 120, e.g., a tumor. Other delivery approaches may be used that do not require the anchoring portion 210 to be passed through the target tissue 120. For example, the anchoring portion may be placed at the periphery of the target tissue. In one embodiment, the proximal end 525 of the cannula 500 has a luer-lockable configuration to facilitate fast connection to a source of liquid chemotherapeutic agent, for example. In FIG. 5D, the cannula 500 is seen to have been directed over the guidewire 520 so that the distal end 530 of the cannula 500 is now within the target tissue 120. Also shown is a source of therapeutic agent 545 connected by a tube 515 to the proximal end of the cannula 500 so that the therapeutic agent 545 can be delivered proximate the target tissue 120. In one embodiment, the distal end of the cannula 530 is tapered to have a "bullet nose" shape to facilitate an easier entry into the target tissue.

In one embodiment, the therapeutic agent is delivered to a target tissue suspected of having tumor cells within lymphovascular tissue proximate a known solid tumor or recently resected solid tumor. The method and system of the present invention allow for chemotherapeutic agents and other tumoricidal agents to be delivered into this tissue suspected of having tumor infiltration of lymphovascular tissue or regional lymph nodes. Thus, the present invention can be used to destroy any tumor cells within the local lymphovascular tiisue, since these lymphatic vessels will "drain" the chemotherapeutic agent in a manner very similar to how they drain the tumor and surrounding tissue of extracellular fluid, eventually leading to lymph nodes. Thus, the system is a useful tool for surgical oncologists and other clinicians to deliver higher concentrations of chemotherapeutic agent (without systemic effects noted in intravenous chemotherapy) to lymphatic tissue near a tumor or recently resected tumor. This higher concentration reduces the chance of tumor cells metastasizing into the nearby lymphovascular system, regional lymph nodes, and eventually the circulatory system.

In either case, once the treatment has been completed, the cannula 500 is removed from the patient by disconnecting the cannula 500 from the source of therapeutic agent 545 and sliding it off of the guide-wire 520. Ideally, the anchoring portion of the guidewire 210 is secured proximate the target tissue 120 so as to not be easily dislodged during treatment. The guidewire 520 should also be easily removed when desired without damaging the tissue. This can be easily accomplished by merely sliding the needle 105 over the guidewire 520 again so that the anchoring portion 210 is now within the lumen 150 of the needle 105. In this state, the surgeon need only remove the needle 105 and guidewire 520 simultaneously.

If an additional treatment with chemotherapy is desired, the guidewire 520 can be left in the patient until the next treatment. In one embodiment, a conventional valve, for example, a 2-way, 3-way, or 4-way stopcock type luer lock (not shown), is connected to the attachment port 540 to control entry of therapeutic agents into the cannula. In one embodiment, a peristaltic pump is used to control the rate of fluid into the patient. The non-anchoring portion 215 of the guidewire 520 can be secured to the patient with a clip or piece of tape with or without antimicrobial activity. Other devices such as a "BioPatch™" (Ethicon, Somerville, N.J.) may also be used to reduce the risk of infection at the site where the guidewire 520 exits the patient. In one embodiment, at least a portion of the guidewire 520 is echogenic, so as to facilitate monitoring of its position relative to the target tissue throughout the course of therapy by ultrasonic imaging. In one embodiment, at least a portion of the guidewire 520 is radiopaque, so as to facilitate monitoring of its position relative to the target tissue throughout the course of therapy by radiographic imaging.

Figure 12A:
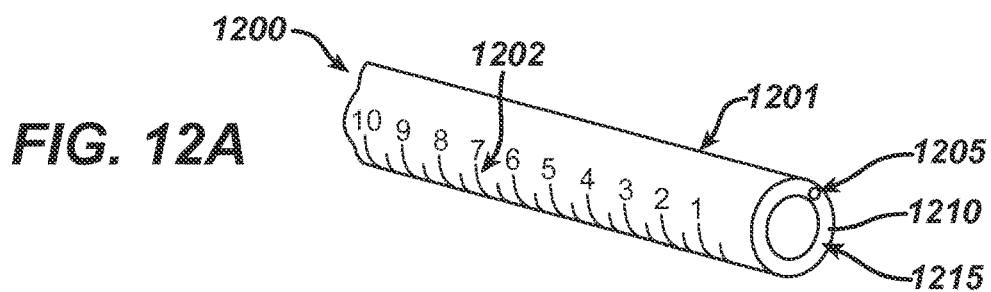
FIGS. 12A-12E are partial perspective views of various cannula constructions having a guidewire lumen useful in the systems of the present invention, and having outer markings on the cannulas.
Figure 12B:
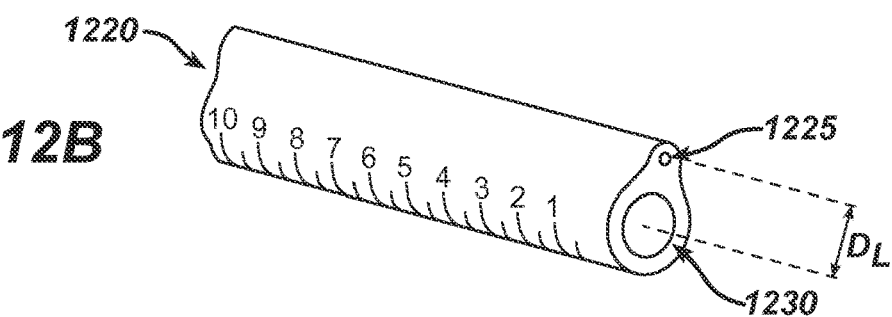
Figure 12C:
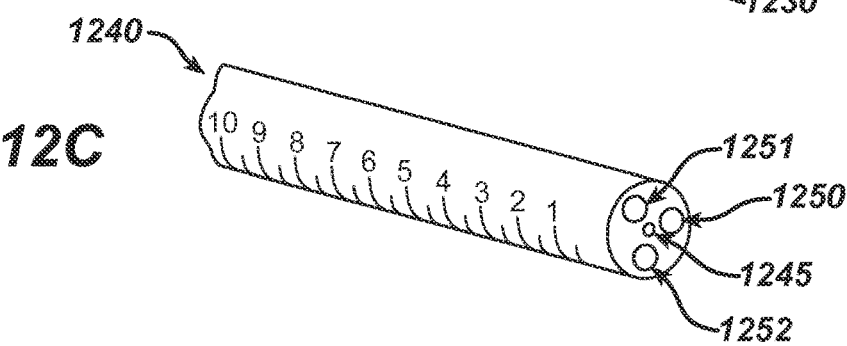
Figure 12D:
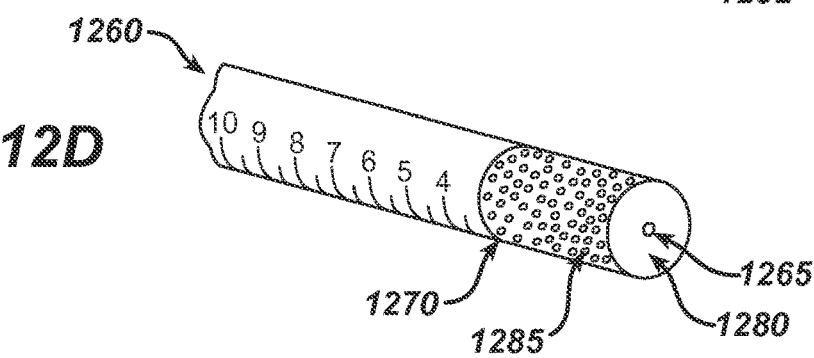
Figure 12E:
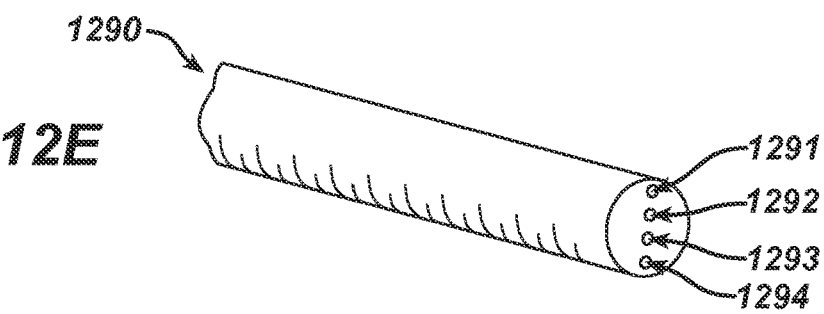

Other suitable configurations of cannula suitable for the system and method are illustrated in FIGS. 12A-E. FIG. 12A illustrates the distal end of a cannula 1200 having a two lumens. Lumen 1205 is used for a guidewire and is located within the wall 1210 of the cannula 1200. Lumen 1215 is fluidly coupled to a source of therapeutic agents (not shown) used for delivery of chemotherapeutic agents, biologic agents, radioactive implants, and agents such as dyes, ethanol, and radiosensitizers. In one embodiment, the sidewall 1201 of the distal end of the cannula 1200 is marked with equally spaced apart markings 1202 to help ascertain how deep the cannula is being placed within the patient or target tissue. These markings may be in increments of millimeters, centimeters or inches and fractions thereof and may include numerical information to aid in knowing how far the cannula has been advanced into the patient. In one embodiment, these markings are lines measured from the proximal end of the cannula. In one embodiment, these markings are measured from the distal end of the cannula. FIG. 12B illustrates the distal end of a cannula 1220 having a guidewire lumen 1225 slightly offset a distance $D_L$ from a larger diameter lumen 1230 of the cannula 1220. Distance $D_L$ can range from 1-20 mm. Lumen 1230 may be fluidly coupled to a source of therapeutic agents (not shown) used for delivery of chemotherapeutic agents, biologic agents, radiative implants, and agents such as ethanol, dyes and radiosensitizers. A radiosensitizer is a drug that makes tumor cells more sensitive to radiation therapy. One of the major limitations of radiotherapy is that the cells of solid tumors become deficient in oxygen. Solid tumors can outgrow their blood supply, causing a low-oxygen state known as hypoxia. Oxygen is a potent radiosensitizer, increasing the effectiveness of a given dose of radiation by forming DNA-damaging free radicals. Tumor cells in a hypoxic environment may be as much as two to three times more resistant to radiation damage than those in a normal oxygen environment. Attempts to overcome this problem include the use of high pressure oxygen tanks, blood substitutes that carry increased oxygen, hypoxic cell radiosensitizers such as misonidazole and metronidazole, and hypoxic cytotoxins, such as tirapazamine. Another approach involves the use of an oxygen diffusion enhancing compound such as trans-sodium crocetinate to re-oxygenate hypoxic tumor tissue. Having the offset configuration on the cannula 1220 enables a larger lumen and a larger diameter guidewire without requiring a thick walled cannula. Another benefit of the offset configuration is that the cannula can be rotated about the axis of a guidewire that has been anchored in a target tissue. Thus, a larger site or multiple sites can be treated. FIG. 12C illustrates the distal end of a cannula 1240, wherein the guidewire lumen 1245 is centrally placed within the cannula 1240. Lumens 1250, 1251, and 1252 can be used to deliver therapeutic agents to three different sites proximate the target tissue. In one embodiment, two or more therapeutic agents can be delivered simultaneously to the target tissue. This can be accomplished by configuring the lumens so that each lumen is fluidly coupled to a different source of therapeutic agent located at the proximal end of the cannula (not shown). For example, one lumen 1250 can serve as the route to deliver a first therapeutic agent, and lumen 1251 can serve as the route to deliver a second therapeutic agent. The third lumen, 1252 can be used to deliver a radiosensitizer to enhance any subsequent radiotherapy or deliver a radiopaque fluid to confirm placement of the cannula proximate a target tissue. In one embodiment, the three lumens can be used to for other functions such as delivery of agents, suction of fluids, or a channel for a biopsy device. FIG. 12D illustrates a cannula 1260 for delivery of chemotherapeutic or biologic agents from the sidewall 1270 of the cannula. In one embodiment, the cannula 1260 has only a lumen 1265 for a guidewire (not shown). Solutions of therapeutic agent are blocked from leaving the tip of the cannula and must exit through a plurality of small channels or pores 1285 located at the distal portion of the cannula 1260. These pores or channels are in fluid communication with a lumen within the cannula (not shown) which is in fluid communication with a source of therapeutic agents located at the proximal end of the cannula (not shown). FIG. 12E illustrates a cannula 1290 having a single lumen 1291 for a guidewire (not shown). It is further comprised of three lumens 1292, 1293, and 1294 for delivery of therapeutic agents and each offset a different distance from the guidewire lumen 1291.

Figure 14:
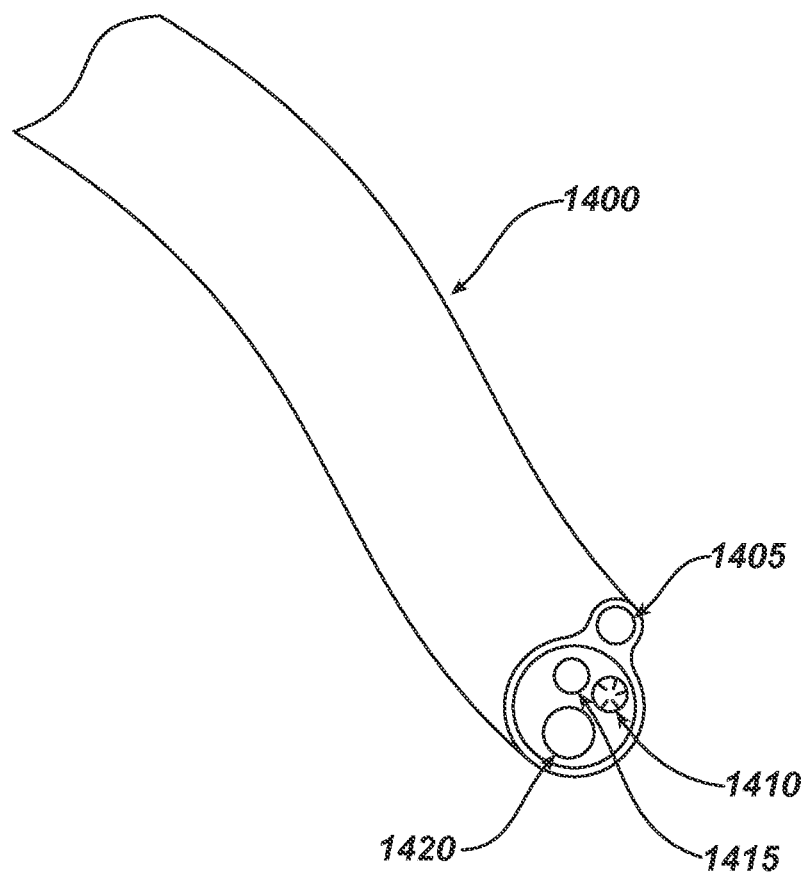
FIG. 14 is a partial perspective view of a cannula having a guidewire lumen, a light source, a camera, and another lumen used to direct therapeutic agents to a target tissue useful in the systems of the present invention.

FIG. 14 illustrates the distal end of a cannula 1400 having a lumen 1405 for a guidewire with anchoring means, a light source 1410, a camera 1415, and a working channel 1420. This incorporation of a light source and camera to the cannula allow a thoracic or general surgeon to actually visualize the delivery of therapeutic agents to a tissue that may not be operable, or to deliver therapeutics to a tissue that is not visible under direct visualization or that has just been debulked.

Figure 6A:
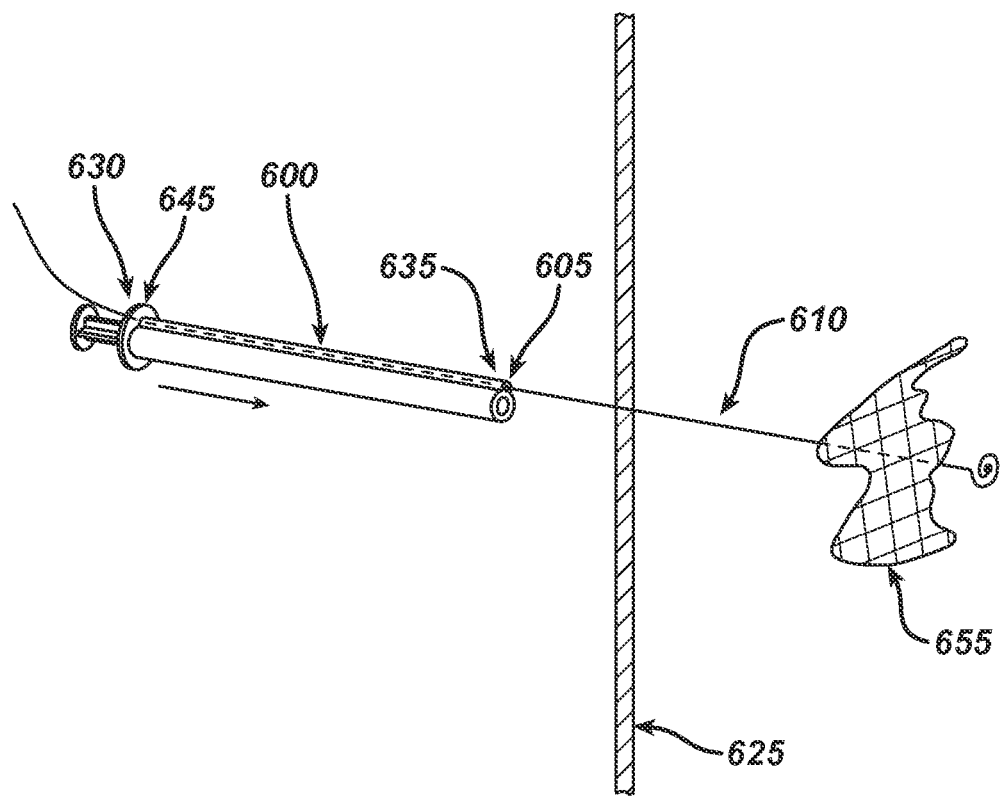
FIG. 6A illustrates a perspective view of a cannula having a small diameter lumen for a guidewire and a larger diameter lumen for radioactive implants; and a schematic of a cannula that is rotatable about a guidewire so as to treat a target tissue such as a tumor with a radioactive implant, a body wall and target tissue are shown in cross-section.
Figure 6B:
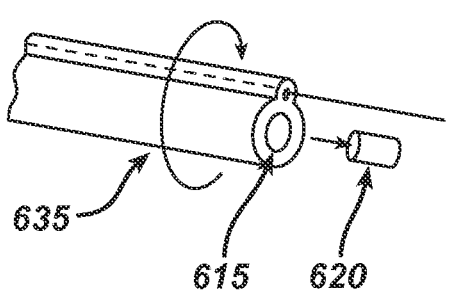
FIG. 6B is a partial perspective view of the cannula of FIG. 6A illustrating a radioactive implant being ejected from the distal end.
Figure 6C:
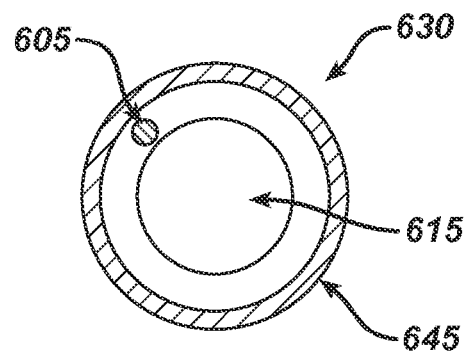
FIG. 6C is a cross-sectional view of the cannula of FIG. 6A.

In one embodiment, the system is used for the placement of radioactive implants or sources in or near the tumor itself, giving a therapeutic radiation dose to the tumor while reducing the radiation exposure in the surrounding healthy tissues. A radioactive implant may be in the form of a seed or pellet and may be selected from typical brachytherapy sourced used in conventional brachytherapy. As shown in FIG. 6A, a cannula 600 having a small diameter lumen 605 for a guidewire 610 and a larger diameter lumen 615 for brachytherapy implants 620 is slidably engaged with the guide-wire 610 that is has been placed across a body wall 625 of the patient's body cavity. In one embodiment, the proximal end 630 of the cannula has an opening to the lumen 615. FIG. 6C illustrates a cross-sectional view of the proximal end 630 of the cannula 600. There is a flange 645 located about the periphery. In one embodiment, the opening to the lumen 615 is large enough to allow for easy placement of at least one radioactive implant 620. Once inside the lumen 615 on the cannula 600, the radioactive implants 620 can be advanced towards the distal end 635 of the cannula 600 and eventually into the target tissue. In one embodiment, the diameter of the lumen 615 is between 0.1-10 mm. The radioactive implants 620 can then be pushed out of the lumen 615 by a push rod 650 that is sized to fit into the lumen 615 of the cannula. FIG. 6B illustrates an embodiment of the present invention in which the cannula 600 is also rotatable about the axis of the guidewire 610, thereby allowing for radioactive implants 620 to be placed at different points and depths proximate the target tissue 655.

Figure 7A:
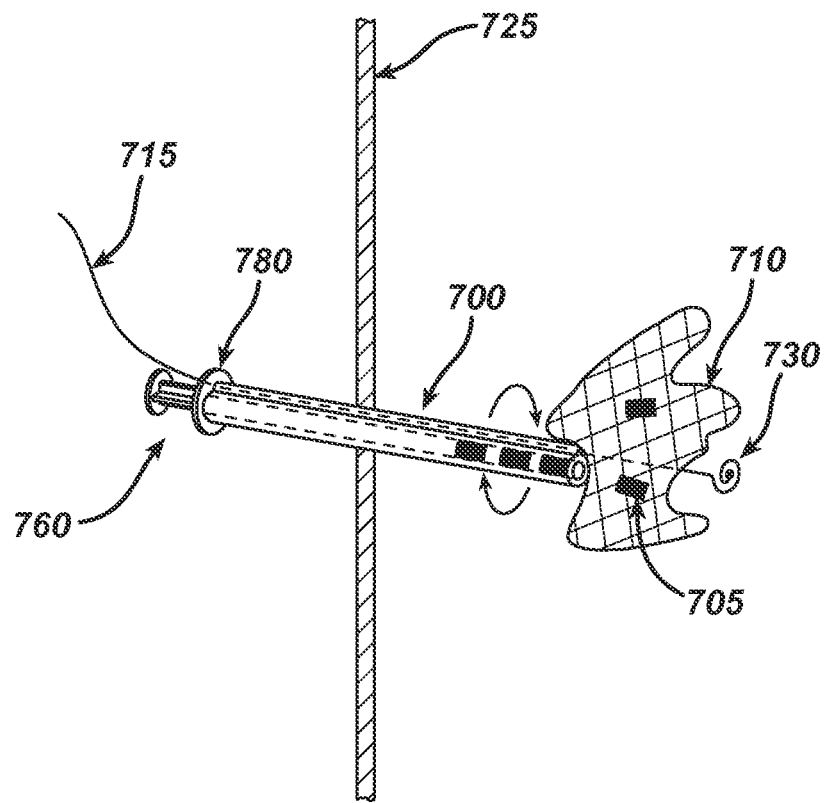
FIG. 7A illustrates radioactive implants being placed within or proximate a target tissue such as a tumor utilizing a system of the present invention, a body wall and the tumor are shown in cross-section.
Figure 7B:
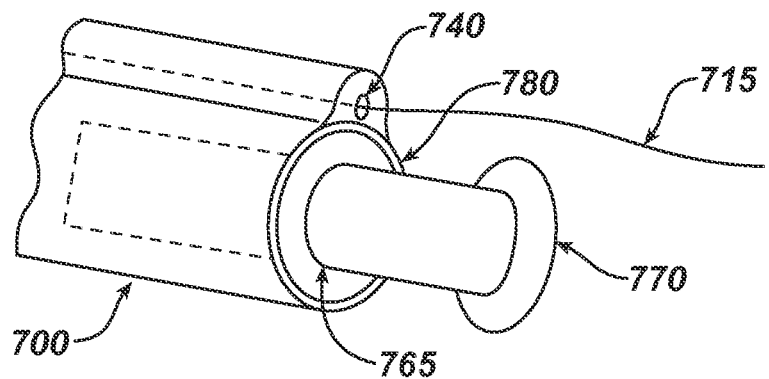
FIG. 7B is a partial, magnified perspective view of the distal end of the cannula of FIG. 7A.

FIGS. 7A-B illustrate the use of this system and method for delivery of radioactive implants 705, or brachytherapy. A guidewire 715 has been placed across a body wall 725 so that the anchoring portion 730 of the guidewire 715 is proximate the target tissue 710. The cannula 700 has been slidably engaged with the guidewire 715 by use of the guidewire lumen 740. As shown in FIG. 7A, a plurality of radioactive implants can be deposited in the lumen of the cannula. Also shown in FIG. 7A is a push rod 770 that is slidably engaged with the lumen 765 of the cannula 700 and can be used to push the implants 705 into the target tissue 710. FIG. 7B is an illustration of the proximal end 760 of the cannula 700. The proximal end has a flange 780 to assist in rotation of the cannula 700, if desired or necessary. The radioactive implants 705 can be placed within or proximate the target tissue 710 with this system. If one or more of the implants 705 are left in the patient, their dose to the target tissue 710 is spread out over a long period of time, with the hope that any cancer cells near the implant 705 are preferentially killed. This is low dose brachytherapy (LDR). The dose rate of brachytherapy refers to the level or 'intensity' with which the radiation is delivered to the surrounding medium and is expressed in Grays/hour (Gy/h). Low-dose rate (LDR) brachytherapy involves implanting radiation sources that emit radiation at a rate of up to 2 Gy/hr. Suitable isotopes to be employed within implants for LDR brachytherapy are iodine (I)-125 and palladium (Pd)-103. With LDR brachytherapy, radiation is delivered at a continuous rate over one to seven days. After the implants 705 have been placed in the target tissue 710, the guidewire 715 and cannula 700 can then be removed from the patient.

In addition to LDR brachytherapy, a higher dose rate (HDR) brachytherapy may be used. In this technique, the implants deliver radiation to the target tissue at a much higher dose rate. In high-dose rate (HDR) brachytherapy, the rate of dose delivery typically exceeds 12 Gy/hr. Suitable isotopes for HDR brachytherapy is iridium (Ir)-192, which provides a higher dose of radiation than the iodine (I)-125 and palladium (Pd)-103. In one embodiment, the system delivers Ir-192 implants into the target tissue for various durations. The total irradiation time may only be 5-10 minutes. For example, in prostate cancer, high dose brachytherapy (HDR) is commonly delivered in 2 or more fractions of 810 Gy or more, with 6-24 hours between treatments. In the event that HDR brachytherapy is being employed by the systems of the present invention, the proximal end of the cannula is connected to an HDR "after-loader". This machine contains a single highly radioactive iridium implant at the end of a wire. The implant is pushed into the cannula under computer control. The computer controls how long the implant stays in the cannula (dwell time), and where along the cannula it should pause to release its radiation (dwell positions). After delivery of the required dose of radiation to the target tissue, the cannula, radioactive implant, and guidewire are removed from the patient's body.

In one embodiment, the systems of the present invention can be used to enable electroporation of the targeted tissue. The term electroporation is widely used to denote the dramatic phenomena that accompany large transmembrane voltages caused by electrical pulses. Electroporation is the application of controlled direct current (DC) electrical pulses which are applied to living cells and tissues for a short duration of time. The pulse induces a transmembrane potential which causes the reversible breakdown of the cellular membrane. This action results in the permeation or "pore formation" of the cell membrane which allows small molecules (such as dye, oligonucleotides or peptides) and large molecules (such as proteins, DNA and RNA) to be introduced into the cell. During this process the cellular uptake of the molecules continues until the pores close, which can take milliseconds to minutes. Utilizing ultra-short pulsed, but very strong electric fields, nanopores are induced in the phospholipid bilayers that form the cell membranes. It is believed that as the applied electrical field increases, the greater is the perturbation of the phospholipid head groups, which in turn increases the number of water filled pores.

Figure 8:
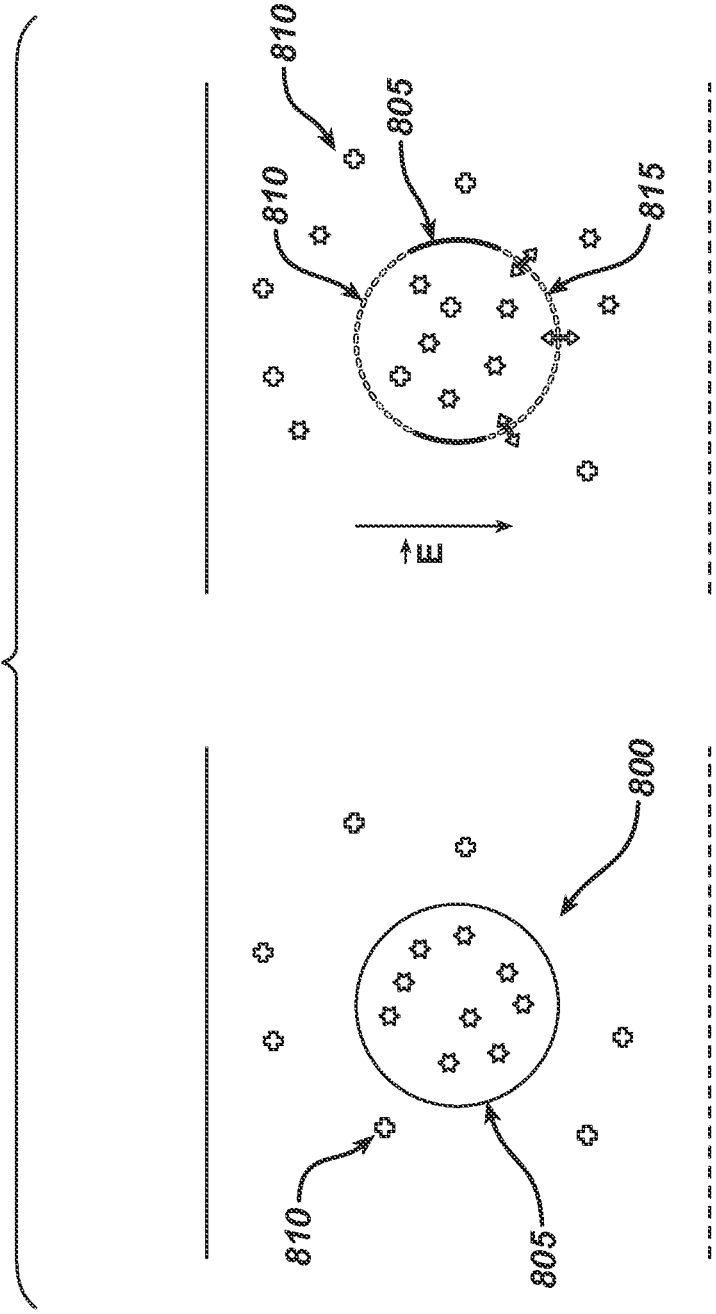
FIG. 8 is a schematic illustrating reversible electroporation used to enhance delivery of drug to a target tissue.

In reversible electroporation (RE), a certain degree of damage induced by nanoporation occurs and the cell can survive. Reversible electroporation is illustrated in FIG. 8, wherein exposure of a cell 800 to an electric field E that can temporarily destabilize the cell membrane 805 during a sufficiently effective period of time. Within this time period, the membrane 805 is highly permeable to exogenous molecules 810 present in the surrounding media. Molecules such as chemotherapeutic or anti-tumor agents can then be delivered into the tumor cells. This procedure is also highly efficient for the introduction of foreign genes in tissue culture cells, especially mammalian cells. When the field E is turned off, the pores 815 in the membrane 805 reseal, enclosing the drug 810 inside. Medical applications of electroporation include, for example, local introduction of an intracellular cytotoxic pharmaceutical such as bleomycin. Optimization of the electroporation process involves several factors. Choosing the wave form, determining field strength and adjusting pulse length are just a few critical variables. Other parameters which play a crucial role in optimization include cell diameter, DNA concentrations, temperature, and electroporation buffer.

Figure 9A:
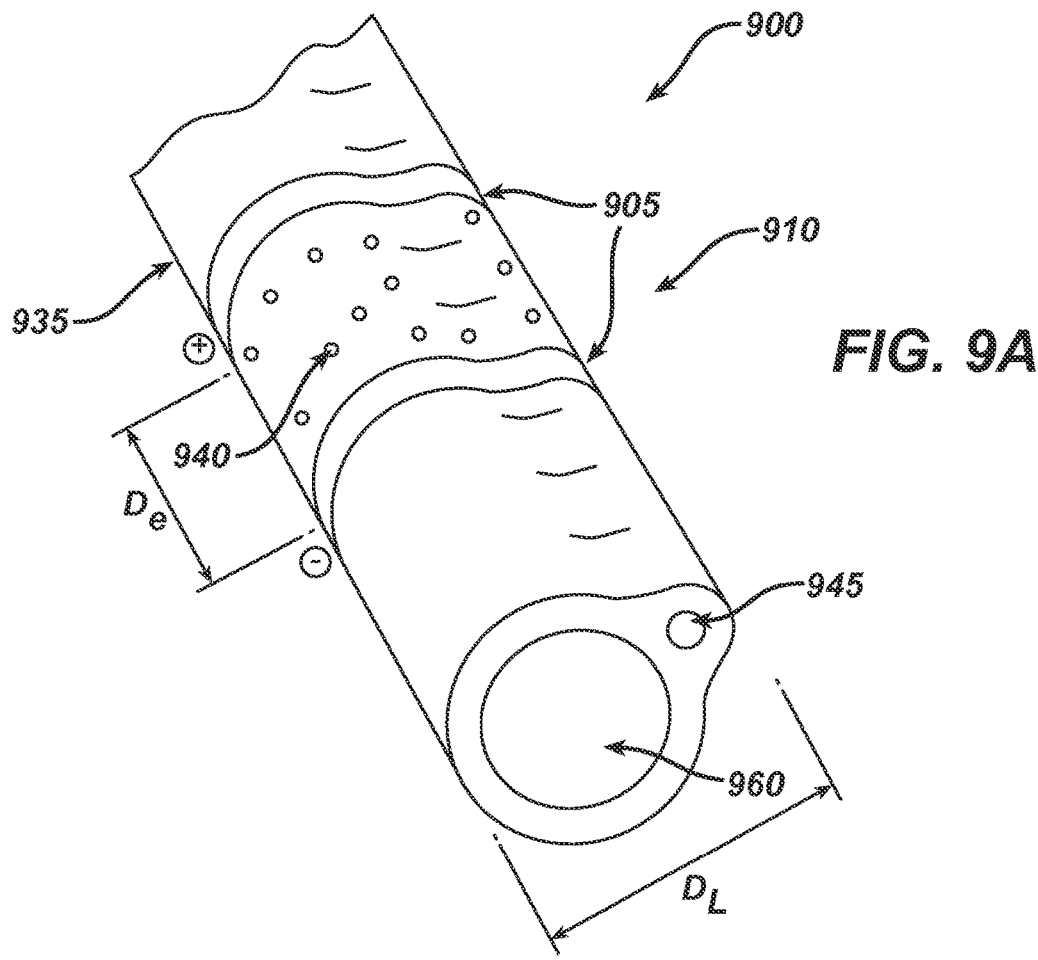
Figure 9B:
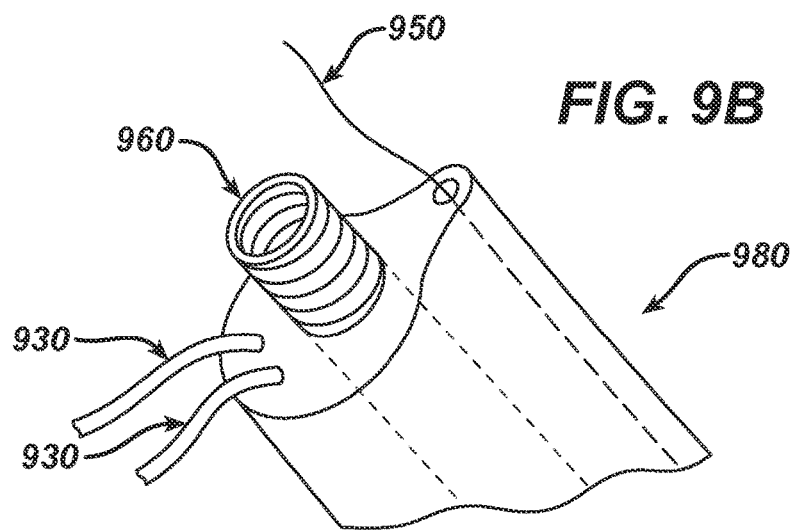

FIGS. 9A-B illustrate one embodiment of the system of the present invention, in which two or more electrodes 905 are present on the distal end 910 of the cannula 900. The electrodes are comprised of a conductive metal such as medical grade stainless steel and comprise an electrically conductive portion (e.g., medical grade stainless steel) and are configured to electrically couple to an energy source. Once the electrodes are positioned into or proximal to the target tissue, an energizing potential is applied to the electrodes to create an electric field to which the target tissue is exposed. The energizing potential (and the resulting electric field) may be characterized by multiple parameters such as frequency, amplitude, pulse width (duration of a pulse or pulse length), and/or polarity. Depending on the diagnostic or therapeutic treatment to be rendered, a particular electrode may be configured either as an anode (+) or a cathode (−) or may comprise a plurality of electrodes with at least one configured as an anode and at least one other configured as a cathode. Regardless of the initial polar configuration, the polarity of the electrodes may be reversed by reversing the polarity of the output of the energy source.

In one embodiment illustrated in FIG. 9A, the distal end of the cannula 910 has two electrodes 905 disposed at a distance $D_e$ from one another. A plurality of pores 940 that communicate between the exterior of the cannula and with the main lumen 960 of the cannula 900 are present between the electrodes 905. The cannula 900 has a lumen 945 for a guidewire 950 and a main lumen 960 that communicates the proximal end 980 of the cannula 900 with the pores 940 located between the electrodes 905. The center of the guidewire lumen 945 is separated from the center of the main lumen by a distance $D_L$. In one embodiment, the proximal end of the cannula 980, shown in FIG. 9B, has one or more insulated conductive leads 930 that conductively communicate with an equal number of electrodes located on the distal end of the cannula 900 by at least two conducting wires 935 to electrodes 905 at the distal end 910 of the cannula 900. Thus, each of the electrodes 905 is connected, via the leads 930, to an energy source such as a DC waveform generator that enables a voltage to be applied to tissue proximate the distal end 910 of the cannula 900. In one embodiment, the generator is an electroporator such as a square wave electroporometer (BTX, Harvard Apparatus) to facilitate electroporation. The system may further comprise a hand piece comprising an activation switch, and an energy source, such as an electrical waveform generator, electrically coupled to the activation switch and the electrodes. The electric field strength employed for the treatment can vary from 0.1-50 kV/cm, depending on the size and geometry of the tissue and the specific tissue involved. In one embodiment, the voltage is applied between the electrodes 905 is at least one pulse having a duration of 1-10,000 microseconds (μsec), depending on the tissue type, tissue size and geometry etc. The electric field strength can be varied during the course of treatment if necessary. The cytotoxic agent, e.g., chemotherapeutic agent, and the buffer it is dissolved in may also influence the choice of pulse width and amplitude of the voltage chosen. The voltage and pulse width are such that it enables to system to induce reversible electroporation near or within the targeted tissue.

FIG. 9C illustrates one embodiment of a cannula 901 useful for the system and method, in which a plurality of electrodes 908 are disposed on the surface 902 of the distal end 921 of the cannula 901. The lumen 903 for a guidewire is centrally disposed at the tip of the distal end 921 of the cannula 901. The proximal end 906 of the cannula 901 is illustrated in FIG. 9D and has at least two insulated conductive leads 911 and 912 that are conductively coupled to the electrodes 908 at the distal end 921 of the cannula 901. As illustrated in FIG. 9C, the electrodes 908 can be alternating positive and negatively charged, thus enabling a bipolar configuration. In one embodiment, the electrodes 908, which may also be referred to as active electrodes, can all have the same, and the opposite charged electrode exists as a grounding pad or return electrode on the surface of the patient's skin, i.e., a monopolar configuration.

Figure 10:
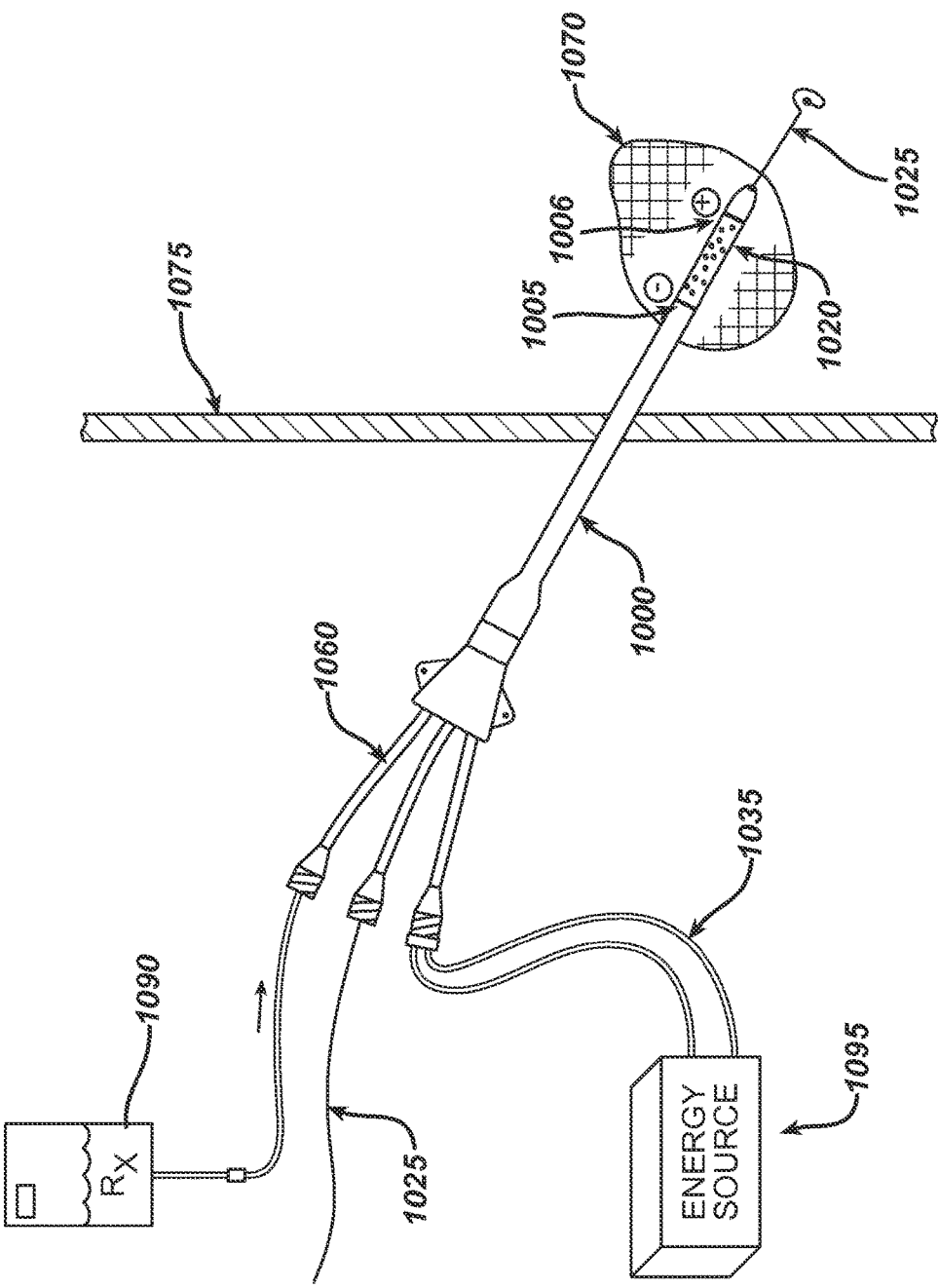
FIG. 10 is an illustration of a system of the present invention with reversible electroporation between two electrodes on a cannula having an energy source and a therapeutic agent source; a body wall and target tissue are shown in cross-section.

FIG. 10 illustrates one embodiment of a system of the present invention used to treat a target tissue 1070 lying within a body cavity 1075 by use of the method and system. The placement of pores 1020 between electrodes 1005 (negative electrode) and 1006 (positive electrode) is particularly useful for reversible electroporation of the target tissue 1070 and the delivery of a chemotherapeutic agent from a source of therapeutic agent 1090 may occur through the main lumen 1060 and pores 1020 of the cannula 1000 which has been advanced over the guidewire 1025. The electrodes are coupled to a conventional energy source such as a generator or electroporator 1095 via insulated wire leads 1035 that extend from the electrodes 1005 and 1006. In one embodiment of the method, the fluid is delivered prior to applying an electric field. In another embodiment, fluid is delivered while the electric field is applied. In one embodiment the fluid is delivered after the electric field is applied. Various frequencies, amplitudes, and waveforms may be used for optimal electroporation of the chemotherapeutic or biological agents. A plurality of electrodes may be placed along the length of the cannula and the cannula may be straight, curved or circular.

In one embodiment, the voltage and pulse width are such that it enables to system to induce irreversible electroporation to tissue proximate the distal end of the cannula. Irreversible electroporation (IRE or NTIRE for non-thermal irreversible electroporation) uses ultra-short, but very strong, electrical fields to create permanent nanopores in the cell membrane that disrupt cellular homeostasis. In irreversible electroporation (IRE), both healthy and cancerous cells are irreversibly damaged. The resulting cell death results from apoptosis, and not necrosis. This is different than all other thermal or radiation based ablation techniques. Although the IRE ablation method is generally accepted to be apoptosis, some findings seem to contradict a pure apoptotic cell death, making the exact process by which IRE causes cell death unclear. The main use of IRE lies in tumor ablation in regions where precision and conservation of the extracellular matrix, blood flow and nerves are of importance.

The geometry of an IRE-treatment field is calculated in real time and can be influenced by the user. Depending on treatment-field and number of electrodes used, the non-thermal ablation enabled by IRE typically takes between 1 to 10 minutes of time. In various embodiments, a series of electrical pulses may be characterized according to the following parameters as may be provided by the energy source. The energy source may be configured to produce direct current (DC) electric pulses at frequencies in the range of about 1 Hz to about 10000 Hz, amplitudes in the range of about ±100 to about ±3000 volts direct current (VDC), and pulse lengths (e.g., pulse width, pulse duration) in the range of about 1 μsec to about 100 milliseconds (msec). The polarity of the electric potentials coupled to the electrodes may be reversed during the electrical ablation therapy. For example, initially, the direct current electric pulses may have a positive polarity and an amplitude in the range of about +100 to about +3000 VDC. Subsequently, the polarity of the DC electric pulses may be reversed such that the amplitude is in the range of about −100 to about −3000 VDC. In one embodiment, the undesirable cells in the target tissue may be electrically ablated with DC pulses suitable to induce irreversible electroporation at frequencies of about 10 Hz to about 100 Hz, amplitudes in the range of about +700 to about +1500 VDC, and pulse lengths of about 10 μs to about 50 μs. It is known to those skilled in the art of electroporation to vary these parameters based on the tissue being treated and the geometry of the tissue. The non-thermal ablation afforded by this system enables treatment of tumor beds previously deemed inoperable by surgeons. For example, prostate carcinomas are frequently located near sensitive regions which might incur permanent damage by thermal treatments or radiation therapy. The applicability of surgical methods is often limited by the accessibility and precision, they have a long healing time and high rate of side effects. Using IRE, the urethra, bladder, rectum, and neurovascular bundle can potentially be included in the treatment field without incurring permanent damage. In addition, the method and system may be particularly useful in the treatment of inoperable pancreatic cancer.

A monopolar configuration for a system of the present invention is illustrated in FIGS. 11A and 11B. The cannula has a single active electrode 1190 placed near the distal tip of the electrode. In one embodiment, the active electrode 1190 is band shaped and has a conductive lead 1192 extending to the proximal end of the cannula where it can be further coupled to the energy source. To complete the circuit, a return electrode in the form of a ground pad (not shown) is located at a distant site on the surface of the patient's body and back to the energy source. In the monopolar configuration, the active electrode 1190 is connected via an electrical conductor 1192 on the proximal end of the cannula which further connects to an DC waveform generator such as an electroporator. As shown in FIG. 11A, the cannula 1100 is directed over the guidewire 1180. Upon further advancement of the cannula over the guidewire into the target tissue, the single electrode 1190 is located proximate the target tissue 1150 as shown in FIG. 11B. Imaging is essential to the placement and can be achieved by ultrasound, magnetic resonance imaging, or computer tomography, i.e., CT. The single electrode 1190 can be a band or net type configuration on the cannula 1100. In one embodiment, the cannula 1100 has a plurality of same charged electrodes all connected to a single hub at the proximal end of the cannula. The electrode or electrodes can be crimped onto the cannula surface, glued onto the cannula, or molded onto the cannula at one or more sites along its length.

When the cannula illustrated in FIGS. 11A-B is coupled to an electric waveform generator such as an electroporator, it can be used for reversible or irreversible electroporation. If the cannula illustrated in FIGS. 11A-B is alternatively coupled to an energy source such as a radiofrequency (RF) generator, it can be used to perform RF ablation of tissue in or near the target tissue via monopolar RF ablation. RF ablation employs the heat generated from high frequency alternating current (in the range of 350-500 kHz) to ablate tissue. Similarly, if an RF generator is used as the energy source, the electrode configurations on the cannulas illustrated in FIGS. 9A-D can be used for bipolar RF ablation. Either system may further comprise a hand piece comprising an activation switch, and an energy source, such as an electrical waveform generator, electrically coupled to the activation switch and the electrodes. Any of the main lumens, i.e., a lumen not used by a guidewire, of cannula illustrated in FIGS. 12A-C, FIG. 12E, or FIG. 14 can be used to deliver straight needle electrodes or "umbrella" or distributed electrodes that are independently coupled to an RF generator.

Figure 15:
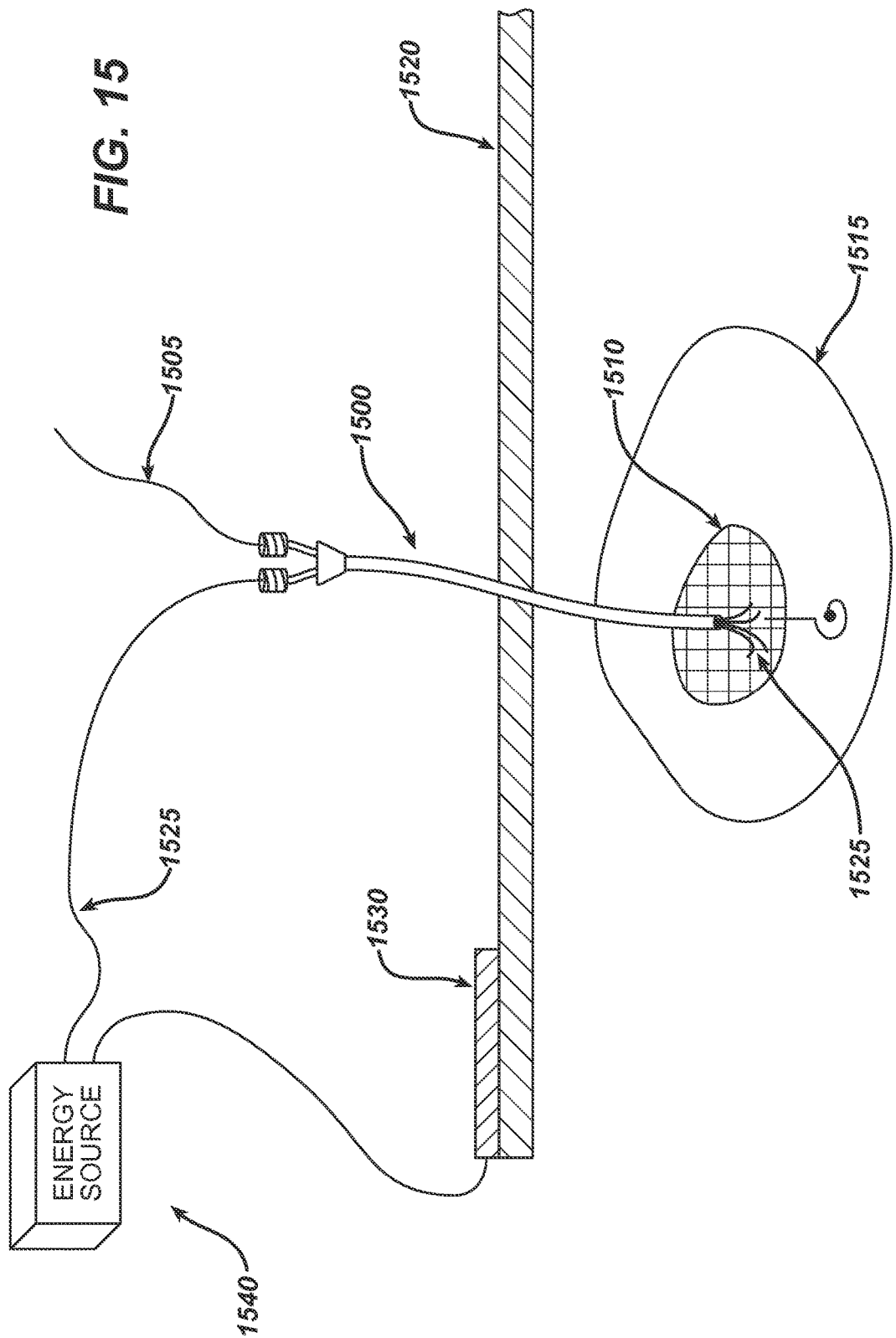
FIG. 15 illustrates delivery of RF energy through a cannula that has been advanced over a guidewire that has been anchored in a target tissue in a system of the present invention; a body wall and target tissue are shown in cross-section.

FIG. 15 illustrates the delivery of RF energy through a cannula 1500 that has been advanced over a guidewire 1505 that has been anchored in a target tissue 1510 within an organ 1515 beneath a body wall 1520 utilizing the system of the present invention. The electrode 1525 that is placed within the target tissue is an umbrella type electrode of one polarity, while an electrode of opposite polarity exists as a grounding pad 1530 on the surface of the patient's body 1520. Both electrodes 1525 and 1530 are coupled to an energy source 1540 such as a conventional RF generator. Thus, a system such as the RF 3000™ (Boston Scientific), which includes a 200W generator and various configurations of straight needle or umbrella electrodes, can be used with any of the RF delivery cannulas illustrated herein. Alternatively a system such as the Cool-tip RF System (Radionics, Burlington, Mass.), consisting of internally cooled electrodes and a 200-W, 480-kHz generator, can be used. The electrodes are introduced into the proximal end of the cannula 1500 and then pushed through the cannula 1500 until they are within or proximate the target tissue. The cannula 1500 is able to deliver the electrodes directly to the target tissue after it has been positioned there by way of the guidewires and methods disclosed herein.

Similarly, other conventional energy-based therapeutic modalities may be introduced through the lumen of the cannulas illustrated in FIGS. 12A-C, FIG. 12E, or FIG. 14. For example, a microwave antenna can be advanced through the lumen of the various guidewire-positioned catheters in FIG. 12A-C, FIG. 12E, or FIG. 14 to deliver microwave energy to a target tissue. Microwave energy can be delivered through tissues and tissue temperatures that present high radiofrequency impedances. This makes microwave energy less susceptible to initial radiofrequency impedance, perfusion and temperature elevation. In one embodiment, a piezo-electric transducer that is coupled to an ultrasound generator can be advanced through the lumen of the guidewire-positioned cannula in FIG. 12A-C, FIG. 12E, or FIG. 14 to deliver high intensity focused ultrasound (HIFU) to a target tissue.

The following example is illustrative of the principles and practices of the present invention, although not limited thereto.

EXAMPLE

A patient suspected of having a metabolic disorder is directed by their doctor to have a ultrasound or CT imaging of their abdomen. For example, a suitable CT scan is obtained by using a 16-detector scanner (Siemens Sensation; Siemens Medical Systems, Erlangen, Germany) and the following technical parameters: 16-section helical acquisition mode, 0.75-mm detector aperture, 0.5-second rotation time, table speed of 3.6 cm/sec, beam pitch of 1.5, 120 kVp, and 130 mAs. A 2 cm suspicious mass is identified within the pancreas. The tumor is considered non-resectable by the surgeon and neoadjuvant therapy comprised of chemotherapy and RF ablation is determined to be the best course of treatment for the patient in that it may shrink the tumor and ablate the remnants, thus avoiding surgery. Rather than expose the patient to systemic chemotherapy, the surgeon chooses to use the system of the present invention.

With the use of the CT scan for guidance, the surgeon plans the access route, completes the sterile skin preparation, and places a local anesthetic in the overlying abdominal wall. Depending on the patient and surgeons wishes, the patient may receive conscious sedation or general anesthesia. The implantation of a localizing wire requires a needle to be inserted into the tissue mass under guidance from an imaging system. Other endoscopic tools may be used to facilitate exposure of the pancreas. Such tools may include insufflation, an endoscope, and various surgical tools need to dissect any tissue that may need to be cleared out of the path of the needle. The needle is positioned with its tip at a selected location proximate the target tissue, i.e., tumor. Once the needle is in place, the guidewire is extended through the needle and out the tip so that the anchoring portion of the guidewire is proximate the tumor. This anchoring step is aided by intra-procedural imaging such as ultrasound and is confirmed when the anchoring portion of the guidewire is seen to be at the desired site. Thereafter, the needle is removed from the target tissue, and the anchoring guidewire remains proximate the tumor. The patient can now be allowed to awake.

The proximal end of a cannula having a lumen for a guidewire and at least one other lumen for a therapeutic agent is then coupled, via a luer-lock fitting, to a source of conventional chemotherapeutic agent, e.g., selected from the group consisting of Gemcitabine (Gemzar®), 5-fluorouracil (5-FU), Irinotecan (Camptosar®), Oxaliplatin (Eloxatin®), Albumin-bound paclitaxel (Abraxane®), Capecitabine (Xeloda®), Cisplatin, Paclitaxel (Taxol®), and Docetaxel (Taxotere®). The therapeutic agent is then allowed to enter the cannula until some of the therapeutic agent is observed to exit the distal end of the cannula. At this point in time, the cannula has been primed with chemotherapeutic agent and the valve or luer-lock fitting between the cannula and source of chemotherapeutic agent is shut off. Using aseptic technique, the surgeon advances the distal end of the cannula over the guidewire until the cannula is observed, via imaging, to be proximate the tumor. The chemotherapeutic agent is allowed, by way of the valve or luer-lock fitting between the cannula and source of chemotherapeutic agent, to be delivered to the tumor and surrounding tissues at a predetermined rate. This rate may vary from 0.01 ml-10 ml per hour, depending on the chemotherapeutic agent chosen, the concentration of the chemotherapeutic agent, and what the surgeon feels is most appropriate for the patient. Means for adjusting the rate of flow may involve adjusting the height of the source of therapeutic agent or the valve if the system is a passive, gravitational based delivery. Alternatively, the surgeon may choose to use a conventional peristaltic pump between the therapeutic source and the cannula to precisely control the flow. After the desired dose of chemotherapeutic agent has been delivered to the patient, the surgeon can decide if the guidewire needs to be removed or if another cycle of therapeutic agent is to be delivered to the target tissue. In either case, it is expected that a portion of the therapeutic agent will be absorbed by the tumor cells and that a portion will be absorbed by normal cells, and that a portion will be absorbed by lymphovascular tissue proximate the target tissue. This latter effect, i.e., absorption by regional lymphovascular vessels, will occur spontaneously if the cannula has not been placed directly within the lumen of a vein or artery and may serve to kill tumor cells that have entered the local lymphovascular system draining the target tissue as well as tumor cells that may migrated to local lymph nodes. Alternatively, the surgeon may choose to treat the target tissue with RF ablation several days after the chemotherapeutic agent has been delivered. During this time, the proximal end of the guidewire can be aseptically secured to the patient's skin with an antimicrobial dressing. After two days, the dressing is removed so that the guidewire can be accessed again. A cannula of the present invention is utilized that is capable of delivering RF energy to a target tissue via a monopolar approach, i.e., the return electrode is on a grounding pad secured to the patient's skin some distance from the operative site, e.g., the patient's thigh. The cannula, having an active electrode on its distal end, is then advanced over the guidewire that is still in place within the patient's pancreas. A suitable dose of RF energy is then delivered to the target tissue and the cannula and grounding pad removed from the patient. Using the appropriate imaging modality, the surgeon then aseptically advances the needle that was used to place the anchoring guidewire back over the guidewire again. The surgeon then advances the needle until the anchoring portion of the guidewire is completely within the lumen of the needle. The guidewire is then removed from the patient by pulling it through the needle until the anchoring portion of the guidewire is outside the needle and patient. The needle is then slowly removed and the small wound remaining on the patient's abdomen is cleaned and bandaged.

The systems and methods of the present invention have numerous advantages and benefits. The advantages and benefits include, but are not limited to enabling localized delivery of therapeutic agents directly to a target tissue such as a tumor while limiting systemic distribution of the therapeutic agents. This enables a higher dose to be delivered to the target tissue while reducing systemic side effects. In addition, the ability to anchor the guidewire in the target tissue while advancing or removing a cannula over it enables repeated administrations of therapeutic agents over a long time period. This allows for less pain to the patient as less needle punctures will be required and it allows for less imaging costs since the tumor has already been anchored into by the guidewire. Furthermore, more than one therapeutic modality can be administered directly to the target tissue simply by changing the cannula type, e.g., use of a cannula of the present invention to deliver chemotherapy followed by use of another cannula of the present invention for delivering radioactive implants proximate the target tissue. Still yet another benefit of the system of the present invention is the ability to bring agents such as radiosensitizers to a target tissue such as a tumor. Radiosensitizers enhance the efficacy subsequent radiotherapy. Still yet another benefit of the system is to deliver chemotherapeutic or biological agents proximate a tumor. These agents may be absorbed by the lymphatic system as well as the tumor. As a result, a means for killing tumor cells within lymphatic vessels and nodes is afforded.

Although this invention has been shown and described with respect to detailed embodiments thereof, it will be understood by those skilled in the art that various changes in form and detail thereof may be made without departing from the spirit and scope of the claimed invention.

We claim:

1. A method of delivering a therapeutic agent to a target tissue, the method comprising:
identifying a target tissue via an imaging modality;
providing a needle having a distal end and a proximal end and a lumen;
inserting the needle into a patient so that its distal end is proximate the target tissue;
inserting a guidewire having a proximal end and a distal end through the lumen of the needle, said guidewire having an anchor member at said distal end;
advancing the guidewire in the lumen so that its distal end is positioned proximate the target tissue;
anchoring said distal end of said guidewire proximate to or in said target tissue using said anchor member;
removing the needle from the patient;
providing a cannula that is removably insertable over said guidewire, said cannula having a proximal end and a distal end and at least first and second lumens therethrough extending between said proximal and distal ends, the cannula having a wall and at least one surface, wherein the cannula is further comprised of two electrodes disposed within the wall of the cannula or on a surface of the cannula at the distal end, wherein the electrodes are disposed on opposed ends of a porous section of the cannula having pores through the cannula wall and wherein said electrodes are coupled to an energy source comprising an electroporator;

removably inserting the proximal end of the guidewire into the first lumens of the cannula and advancing the cannula over the guidewire until the distal end of the cannula is proximate the target tissue;

coupling the second lumen to a source of therapeutic agent at the proximal end of the cannula; and while the guidewire remains in place within the first lumen of the cannula, delivering the therapeutic agent to the target tissue through the second lumen and porous section of the cannula, wherein the target tissue comprises cells, and the therapeutic agent comprises a therapeutic agent selected from the group consisting of monoclonal antibodies, immunoconjugates, cytokines, oncolytic viruses, vaccines, genetic material, antimicrobial agents, antibiotics, steroids, nonsteroidal anti-inflammatory drugs (NSAIDS), vascular endothelial growth factor (VEGF), growth factor (GF), ethanol and radiosensitizers;

delivering reversible electroporation direct current (DC) electric pulses from the electroporator to cause the therapeutic agent to be delivered into the cells or target tissue; and uncoupling the second lumen from the source of therapeutic agent and delivering a second treatment to the target tissue through the second lumen.

2. The method of claim 1, wherein the imaging modality is selected from the group consisting of computer tomography, magnetic resonance imaging, positron emission tomography, fluorography, ultrasound, radioimmunoscintigraphy, radiography, indirect visualization and direct visualization.

3. The method of claim 1, wherein the cannula is further comprised of a light source and a camera.

4. The method according to claim 1, further comprising the steps of:
  removing the cannula from the guidewire, while maintaining the guidewire in place;
  subsequently providing a second cannula having a proximal end and a distal end and at least first and second lumens therethrough extending between said proximal and distal ends,
  inserting the proximal end of the guidewire into the first lumen of the second cannula and advancing the second cannula over the guidewire until the distal end of the second cannula is proximate the target tissue;
  coupling the second lumen of the cannula to a source of therapeutic agent at the proximal end of the second cannula; and
  while the guidewire remains in place within the first lumen of the second cannula, delivering a therapeutic agent to the target tissue through the second lumen of the second cannula.

5. The method according to claim 1, wherein the second treatment comprises delivering a second therapeutic agent selected from the group consisting of a chemotherapeutic agent, biological agent, dye, ethanol, radiosensitizer, radioactive implant, and a fluid with a temperature above 40 degrees Celsius or below minus 20 degrees Celsius.

6. The method according to claim 5, wherein the second therapeutic agent is a biological agent, and wherein the biological agent is selected from the group consisting of monoclonal antibodies, immunoconjugates, cytokines, oncolytic viruses, vaccine, and genetic material.

* * * * *